US012685632B2

(12) United States Patent     (10) Patent No.:   US 12,685,632 B2

Reich et al.         (45) Date of Patent:     Jul. 21, 2026

(54) BELT FOR PROSTHETIC HEART VALVE

(71) Applicant: Edwards Lifesciences Corporation, Irvine, CA (US)

(72) Inventors: Tal Reich, Moledet (IL); Noam Nir, Pardes-Hanna (IL); Ziv Yohanan, Kfar Hahoresh (IL); Tamir S. Levi, Zikhron Yaakov (IL); Michael Bukin, Pardes Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 954 days.

(21) Appl. No.: 17/827,377

(22) Filed: May 27, 2022

(65) Prior Publication Data

US 2022/0287834 A1     Sep. 15, 2022

Related U.S. Application Data

(63) Continuation of application No. PCT/US2020/062212, filed on Nov. 25, 2020.

(Continued)

(51) Int. Cl.
*A61F 2/24*        (2006.01)

(52) U.S. Cl.
CPC .... *A61F 2/2418* (2013.01); *A61F 2230/0091* (2013.01); *A61F 2250/001* (2013.01);
(Continued)

(58) Field of Classification Search
CPC ........ A61F 2/24; A61F 2/2418; A61F 2/2409; A61F 2/2412; A61F 2/2427; A61F 2/243;
(Continued)

(56) References Cited

U.S. PATENT DOCUMENTS

| | | |
|---|---|---|
| 3,409,013 A | 11/1968 | Berry |
| 3,548,417 A | 12/1970 | Kisher |

(Continued)

FOREIGN PATENT DOCUMENTS

| | | | | |
|---|---|---|---|---|
| CA | 2875444 A1 * | 12/2013 | ....... | A61B 17/12118 |
| DE | 0144167 C | 9/1903 | | |

(Continued)

OTHER PUBLICATIONS

H.R. Andersen, et al. "Transluminal Implantation of Artificial Heart Valve, Description of a New Expandable Aortic Valve and Initial Results with implantation by Catheter Technique in Closed Chest Pig," European Heart Journal, No. 13. pp. 704-708. 1992.

(Continued)

*Primary Examiner* — Seema Mathew

(74) *Attorney, Agent, or Firm* — Klarquist Sparkman, LLP

(57) ABSTRACT

A belt for an implantable prosthetic device can include an annular body including a plurality of alternating peaks and valleys and a plurality of frangible members extending between at least one of adjacent peaks and adjacent valleys. The annular body can be radially expandable from a radially compressed configuration to a first diameter upon application of a radially outwardly directed force via an expandable implantable prosthetic device. A first frangible member of the plurality of frangible members can be configured to break when the radially outwardly directed force exceeds a first predetermined threshold to allow radial expansion of the annular body to a second diameter.

14 Claims, 16 Drawing Sheets

Related U.S. Application Data

(60) Provisional application No. 62/945,059, filed on Dec. 6, 2019.

(52) U.S. Cl.
CPC ................ *A61F 2250/0031* (2013.01); *A61F 2250/0071* (2013.01)

(58) Field of Classification Search
CPC ...... A61F 2/2439; A61F 2/2457; A61F 2/246; A61F 2/2463; A61F 2/2466; A61F 2002/9534; A61F 2/90; A61F 2/92; A61F 2/02; A61F 2250/007
See application file for complete search history.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,779,732 A * | 7/1998 | Amundson | A61F 2/958 606/198 |
| 5,800,508 A | 9/1998 | Goicoechea et al. | |
| 5,840,081 A | 11/1998 | Andersen et al. | |
| 5,843,158 A | 12/1998 | Lenker et al. | |
| 5,855,597 A | 1/1999 | Jayaraman | |
| 5,855,601 A | 1/1999 | Bessler et al. | |
| 5,855,602 A | 1/1999 | Angell | |
| 5,873,906 A * | 2/1999 | Lau | A61F 2/92 606/198 |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goecoechea et al. | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |

(56)                    References Cited

U.S. PATENT DOCUMENTS

| | | | |
|---|---|---|---|
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,011,682 B2 * | 3/2006 | Lashinski | A61F 2/2466 |
| | | | 623/2.37 |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,167,932 B2 | 5/2012 | Bourang et al. | |
| 8,291,570 B2 | 10/2012 | Eidenschink et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,690,897 B2 * | 4/2014 | Bolduc | A61F 2/0095 |
| | | | 606/139 |
| 8,747,463 B2 | 6/2014 | Fogarty et al. | |
| 8,968,384 B2 * | 3/2015 | Pearson | A61F 2/954 |
| | | | 623/1.13 |
| 9,078,781 B2 | 7/2015 | Ryan et al. | |
| 9,254,209 B2 * | 2/2016 | Shalev | A61F 2/064 |
| 9,597,204 B2 * | 3/2017 | Benary | A61F 2/856 |
| 11,224,509 B2 | 1/2022 | Dasi et al. | |
| 11,234,812 B2 * | 2/2022 | Green | A61F 2/2418 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0039436 A1 | 2/2004 | Spenser et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |

| | | | |
|---|---|---|---|
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0243245 A1 | 10/2008 | Thambar et al. | |
| 2008/0275537 A1 | 11/2008 | Limon | |
| 2008/0294234 A1 * | 11/2008 | Hartley | A61F 2/954 |
| | | | 623/1.13 |
| 2009/0125118 A1 | 5/2009 | Gong | |
| 2009/0157175 A1 | 6/2009 | Benichou | |
| 2009/0216308 A1 * | 8/2009 | Hartley | A61F 2/95 |
| | | | 623/1.11 |
| 2009/0276040 A1 | 11/2009 | Rowe et al. | |
| 2009/0281619 A1 | 11/2009 | Le et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0168844 A1 | 7/2010 | Toomes et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0264192 A1 * | 10/2011 | Hartley | A61F 2/07 |
| | | | 623/1.13 |
| 2011/0319991 A1 | 12/2011 | Hariton et al. | |
| 2012/0071921 A1 * | 3/2012 | Shanley | A61B 90/06 |
| | | | 606/232 |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2013/0023985 A1 | 1/2013 | Khairkhahan et al. | |
| 2013/0046371 A1 * | 2/2013 | Greenberg | A61F 2/95 |
| | | | 623/1.11 |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0031930 A1 * | 1/2014 | Keidar | A61F 2/2433 |
| | | | 623/2.37 |
| 2014/0148888 A1 * | 5/2014 | Barrand | A61F 2/07 |
| | | | 623/1.2 |
| 2014/0148895 A1 * | 5/2014 | King | A61F 2/07 |
| | | | 623/1.13 |
| 2014/0180378 A1 * | 6/2014 | Roeder | A61F 2/07 |
| | | | 623/1.13 |
| 2014/0188221 A1 | 7/2014 | Chung et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0366664 A1 * | 12/2015 | Guttenberg | A61F 2/2418 |
| | | | 623/2.17 |
| 2016/0045312 A1 * | 2/2016 | Braido | A61B 5/02028 |
| | | | 623/2.37 |

(56) References Cited

U.S. PATENT DOCUMENTS

| | | | | |
|---|---|---|---|---|
| 2017/0165067 A1* | 6/2017 | Barajas-Torres | ...... | A61F 2/2418 |
| 2017/0273784 A1* | 9/2017 | Racchini | ............... | A61F 2/2412 |
| 2021/0228389 A1* | 7/2021 | Smith | ..................... | A61F 2/966 |
| 2025/0127616 A1* | 4/2025 | Nir | ......................... | A61F 2/2418 |
| 2026/0047927 A1* | 2/2026 | Maimon | ............... | A61F 2/2418 |

FOREIGN PATENT DOCUMENTS

| | | | | | |
|---|---|---|---|---|---|
| DE | 2246526 | A1 | 3/1973 | | |
| DE | 19532846 | A1 | 3/1997 | | |
| DE | 19546692 | A1 | 6/1997 | | |
| DE | 19857887 | A1 | 7/2000 | | |
| DE | 19907646 | A1 | 8/2000 | | |
| DE | 10049812 | A1 | 4/2002 | | |
| DE | 10049813 | C1 | 4/2002 | | |
| DE | 10049814 | A1 | 4/2002 | | |
| DE | 10049815 | A1 | 4/2002 | | |
| EP | 0103546 | A1 | 3/1984 | | |
| EP | 0850607 | A1 | 7/1998 | | |
| EP | 1057460 | A1 | 12/2000 | | |
| EP | 1088529 | A2 | 4/2001 | | |
| EP | 1570809 | A1 | 9/2005 | | |
| FR | 2788217 | A1 | 7/2000 | | |
| FR | 2815844 | A1 | 5/2002 | | |
| GB | 2056023 | A | 3/1981 | | |
| SU | 1271508 | A1 | 11/1986 | | |
| WO | 9117720 | A1 | 11/1991 | | |
| WO | 9217118 | A1 | 10/1992 | | |
| WO | 9301768 | A1 | 2/1993 | | |
| WO | 9724080 | A1 | 7/1997 | | |
| WO | WO-9725002 | A1 * | 7/1997 | ............... | A61F 2/90 |
| WO | 9829057 | A1 | 7/1998 | | |
| WO | 9930646 | A1 | 6/1999 | | |
| WO | 9933414 | A1 | 7/1999 | | |
| WO | 9940964 | A1 | 8/1999 | | |
| WO | 9947075 | A1 | 9/1999 | | |
| WO | 0018333 | A1 | 4/2000 | | |
| WO | 0041652 | A1 | 7/2000 | | |
| WO | 0047139 | A1 | 8/2000 | | |
| WO | 0135878 | A2 | 5/2001 | | |
| WO | 0149213 | A2 | 7/2001 | | |
| WO | 0154624 | A1 | 8/2001 | | |
| WO | 0154625 | A1 | 8/2001 | | |
| WO | 0162189 | A1 | 8/2001 | | |
| WO | 0164137 | A1 | 9/2001 | | |
| WO | 0176510 | A2 | 10/2001 | | |
| WO | 0222054 | A1 | 3/2002 | | |
| WO | 0236048 | A1 | 5/2002 | | |
| WO | 0241789 | A2 | 5/2002 | | |
| WO | 0243620 | A1 | 6/2002 | | |
| WO | 0247575 | A2 | 6/2002 | | |
| WO | 0249540 | A2 | 6/2002 | | |
| WO | 03047468 | A1 | 6/2003 | | |
| WO | 2005034812 | A1 | 4/2005 | | |
| WO | 2005055883 | A1 | 6/2005 | | |
| WO | 2005084595 | A1 | 9/2005 | | |
| WO | 2005102015 | A2 | 11/2005 | | |
| WO | 2006014233 | A2 | 2/2006 | | |
| WO | 2006032051 | A2 | 3/2006 | | |
| WO | 2006034008 | A2 | 3/2006 | | |
| WO | 2006111391 | A1 | 10/2006 | | |
| WO | 2006127089 | A1 | 11/2006 | | |
| WO | 2006138173 | A2 | 12/2006 | | |
| WO | 2007047488 | A2 | 4/2007 | | |
| WO | 2007067942 | A1 | 6/2007 | | |
| WO | 2007097983 | A2 | 8/2007 | | |
| WO | 2008005405 | A2 | 1/2008 | | |
| WO | 2008015257 | A2 | 2/2008 | | |
| WO | 2008035337 | A2 | 3/2008 | | |
| WO | 2008091515 | A2 | 7/2008 | | |
| WO | 2008147964 | A1 | 12/2008 | | |
| WO | 2008150529 | A1 | 12/2008 | | |
| WO | 2009033469 | A1 | 3/2009 | | |
| WO | 2009042196 | A2 | 4/2009 | | |
| WO | 2009053497 | A1 | 4/2009 | | |
| WO | 2009061389 | A2 | 5/2009 | | |
| WO | 2009094188 | A2 | 7/2009 | | |
| WO | WO-2009102441 | A1 * | 8/2009 | ............... | A61F 2/07 |
| WO | 2009116041 | A2 | 9/2009 | | |
| WO | 2009149462 | A2 | 12/2009 | | |
| WO | 2010011699 | A2 | 1/2010 | | |
| WO | WO-2010033931 | A2 | 3/2010 | | |
| WO | WO-2010033936 | A2 | 3/2010 | | |
| WO | 2010121076 | A2 | 10/2010 | | |
| WO | 2013106585 | A1 | 7/2013 | | |
| WO | WO-2014179763 | A1 | 11/2014 | | |
| WO | 2015085218 | A1 | 6/2015 | | |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

* cited by examiner

1

BELT FOR PROSTHETIC HEART VALVE

CROSS REFERENCE TO RELATED APPLICATION

This application is a continuation of a PCT Patent Application No. PCT/US2020/062212, entitled "BELT FOR PROSTHETIC HEART VALVE," filed Nov. 25, 2020, which claims the benefit of U.S. Provisional Application No. 62/945,059, entitled "BELT FOR PROSTHETIC HEART VALVE" filed on Dec. 6, 2019, all of which are incorporated by reference herein in their entirety.

FIELD

The present disclosure relates to implantable, mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Prosthetic heart valves that rely on a mechanical actuator for expansion can be referred to as "mechanically expandable" prosthetic heart valves. Mechanically expandable prosthetic heart valves can provide one or more advantages over self-expandable and balloon-expandable prosthetic heart valves. For example, mechanically expandable prosthetic heart valves can be expanded to various diameters. Mechanically expandable prosthetic heart valves can also be compressed after an initial expansion (e.g., for repositioning and/or retrieval).

When deploying a prosthetic valve, it is important to avoid exerting excessive radial force on the native annulus of the patient, which can rupture the native heart valve annulus. To avoid damage to the native tissue, it is desirable to monitor the diameter of the prosthetic valve and/or the radial force exerted by the prosthetic valve during deployment.

Unfortunately, known methods for measuring diameter and radial force suffer from several problems. For example, measurement methods relying on measuring the displacement of an actuation mechanism fail to account for factors such as compression of the delivery device and/or elongation of the actuation mechanism under tension. Thus, despite the recent advancements in percutaneous valve technology, there remains a need for improved devices and methods for monitoring the diameter and radial force of transcatheter heart valves during implantation.

SUMMARY

In a representative embodiment, a belt for an implantable prosthetic device can comprise an annular body including a plurality of alternating peaks and valleys and a plurality of frangible members extending between at least one of adjacent peaks and adjacent valleys. The annular body can be radially expandable from a radially compressed configuration to a first diameter upon application of a radially outwardly directed force via an expandable implantable prosthetic device. A first frangible member of the plurality of frangible members can be configured to break when the radially outwardly directed force exceeds a first predetermined threshold to allow radial expansion of the annular body to a second diameter.

In another representative embodiment, an assembly can comprise an implantable prosthetic device comprising a frame movable between a radially compressed configuration and a radially expanded configuration, and a belt extending circumferentially around the frame. The belt can be configured to radially expand to a first diameter when a first force below a predetermined threshold is applied and expand to a second diameter when a second force greater than the predetermined threshold is applied.

In a representative embodiment, a method can comprise advancing an implantable prosthetic device comprising a belt to a selected implantation site inside the body of a patient, the belt extending around a circumference of the prosthetic device and comprising one or more frangible members, and radially expanding the prosthetic device and the belt to a first diameter. The method can further comprise applying a first expansion force greater than a predetermined threshold to the prosthetic valve to break a first frangible member, and radially expanding the prosthetic device and the belt to a second diameter.

In another representative embodiment, an implantable prosthetic device can comprise a frame movable between a radially compressed configuration and a radially expanded configuration, the frame having an inflow end portion and an outflow end portion, and a restriction band extending circumferentially around the frame. The restriction band can be configured to allow expansion of the frame to a selected diameter and to prevent expansion of the frame past the selected diameter.

In a representative embodiment, a method can comprise determining a selected maximum diameter for an implantable prosthetic device based at least in part on a patient's native anatomy. The prosthetic device can comprise a plurality of restriction belts extending around a circumference of the frame, each belt having a different maximum diameter. The method can further comprise cutting any of the plurality of restriction belts having a maximum diameter less than the selected maximum diameter, advancing the implantable prosthetic device to a selected implantation site inside the body of the patient, and radially expanding the prosthetic device and the remaining restriction belts to the selected maximum diameter.

In another representative embodiment, an implantable prosthetic device can comprise a frame movable between a radially compressed configuration and a radially expanded configuration, the frame having an inflow end portion and an outflow end portion, and a tension member extending circumferentially around at least a portion of the frame, the tension member having a first end portion releasably coupled to the frame and a second end portion configured to be coupled to a handle of a delivery apparatus. The tension member can apply a radially inwardly directed force to the frame that can be gradually lessened such that the frame can expand at a controlled rate to a selected diameter.

In a representative embodiment, a method can comprise inserting a distal end of a delivery apparatus into the vasculature of a patient. The delivery apparatus can be releasably coupled to an implantable prosthetic device comprising a frame and a tension member extending circumferentially around at least a portion of the frame. The tension member can have a first end portion releasably coupled to the frame and a second end portion configured to be coupled to a handle of the delivery apparatus. The method can further comprise advancing the prosthetic valve to a selected implantation site, tensioning the tension member to retain the frame in a radially compressed configuration, retracting a sheath of the delivery apparatus to expose the implantable prosthetic device, and radially expanding the prosthetic device while gradually releasing the tension in the tension member to allow the prosthetic valve to expand at a controlled rate.

In another representative embodiment, a method comprises determining a first selected maximum diameter for an inflow end portion and a second selected maximum diameter for an outflow end portion of an implantable prosthetic device based at least in part on a patient's native anatomy. The prosthetic device comprising a frame having first restriction band extending around a circumference of the frame at the inflow end portion and a second restriction band extending around the circumference of the frame at the outflow end portion. The method further comprises releasing the first restriction band such that it is expandable to the first selected maximum diameter, releasing the second restriction band such that it is expandable to the second selected maximum diameter, advancing the implantable prosthetic device to a selected implantation site inside the body of the patient, and radially expanding the prosthetic device such that the inflow end portion is at the first selected maximum diameter and the outflow end portion is at the second selected maximum diameter.

The foregoing and other objects, features, and advantages of the disclosure will become more apparent from the following detailed description, which proceeds with reference to the accompanying figures.

4

Figures 3, 4:
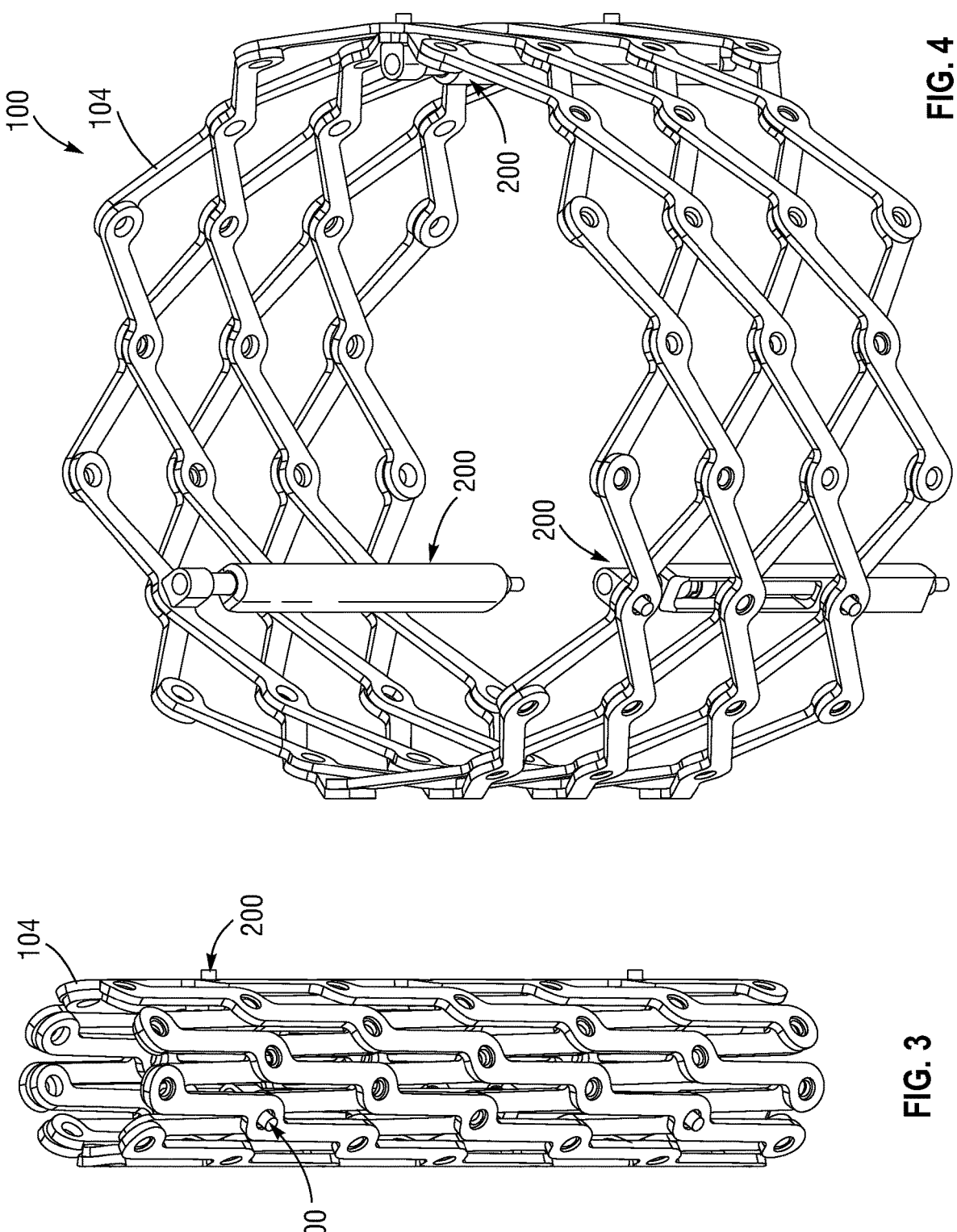
FIG. 3 is a perspective view of a prosthetic valve frame, shown in a radially collapsed state, having a plurality of expansion and locking mechanisms, according to another embodiment.
FIG. 4 is a perspective view of the frame and the expansion and locking mechanisms of FIG. 3, with the frame shown in a radially expanded state.
Figure 5C:
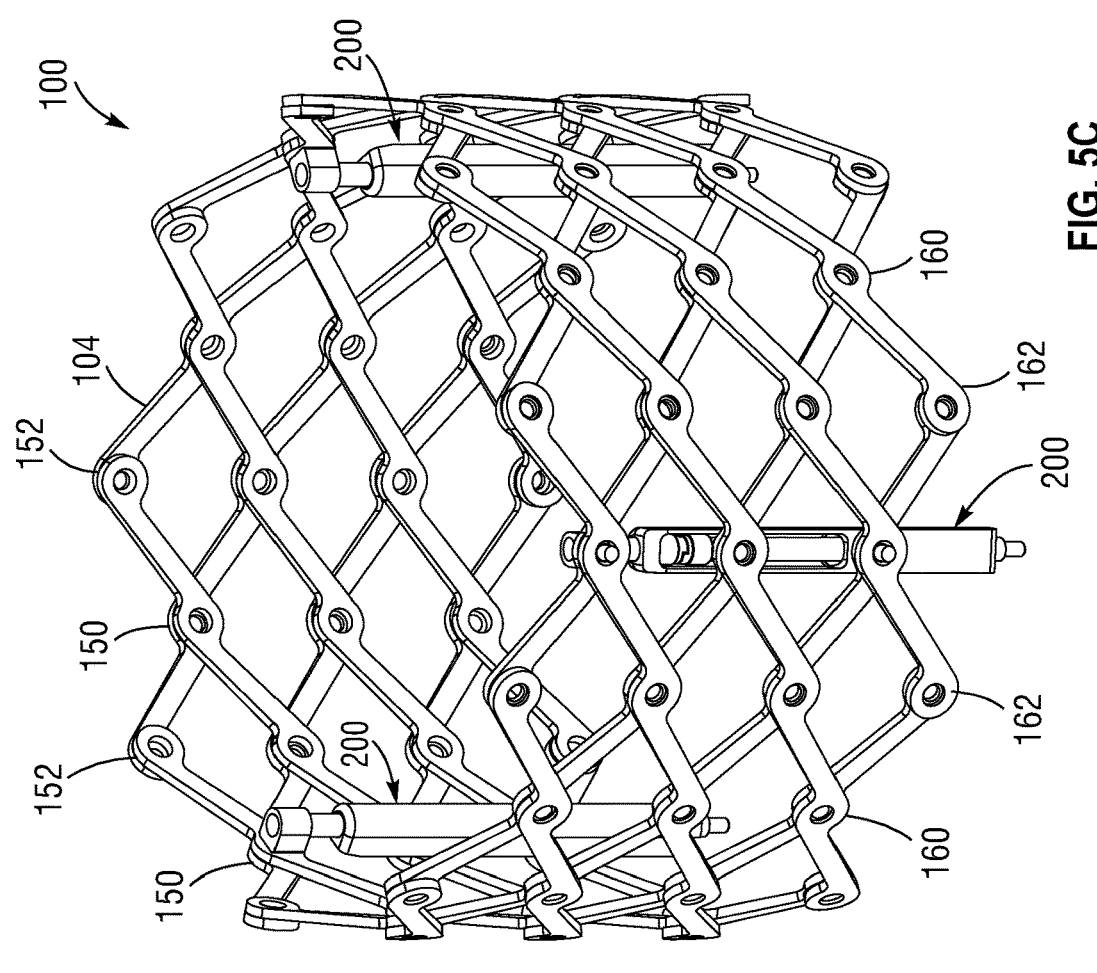
Figure 5B:
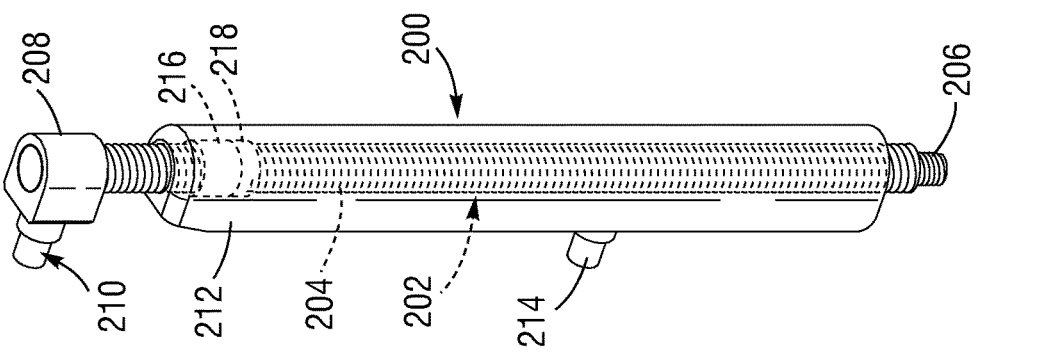
Figure 5A:
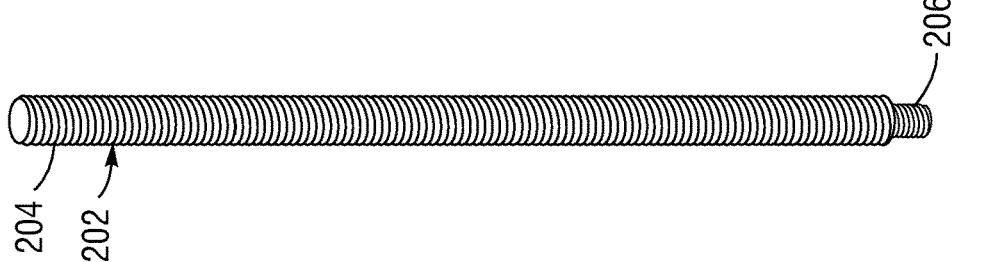

FIG. 5A is a perspective view of a screw of one of the expansion and locking mechanisms of FIG. 3, FIG. 5B is a perspective view of one of the expansion and locking mechanisms of FIG. 3.

FIG. 5C is another perspective view of the frame and the expansion and locking mechanisms of FIG. 3, with the frame shown in a radially expanded state.

Figure 6:
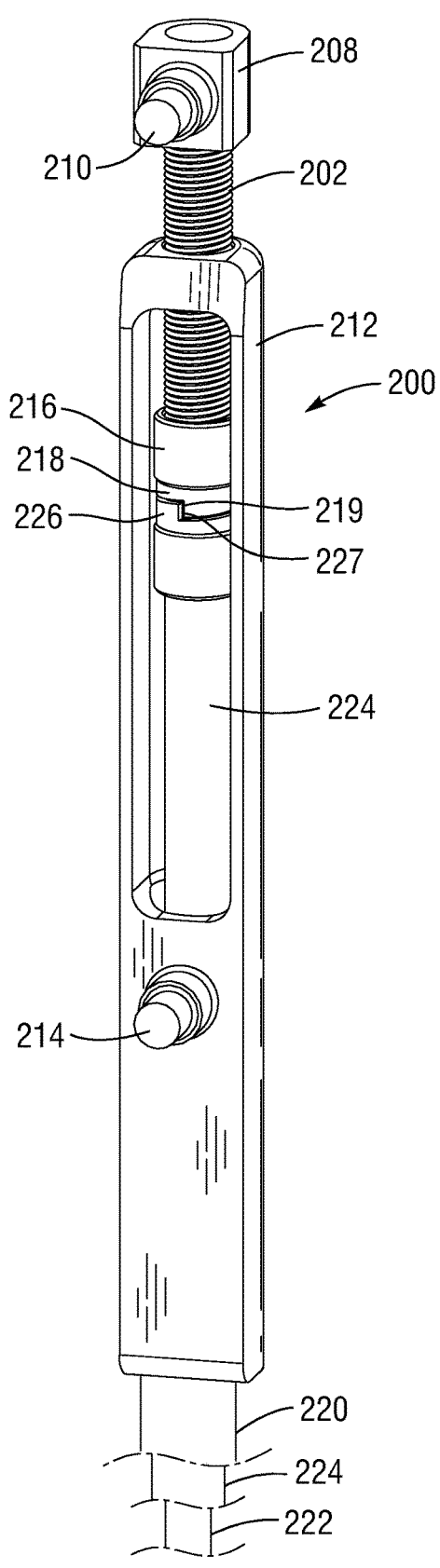
Figure 7:
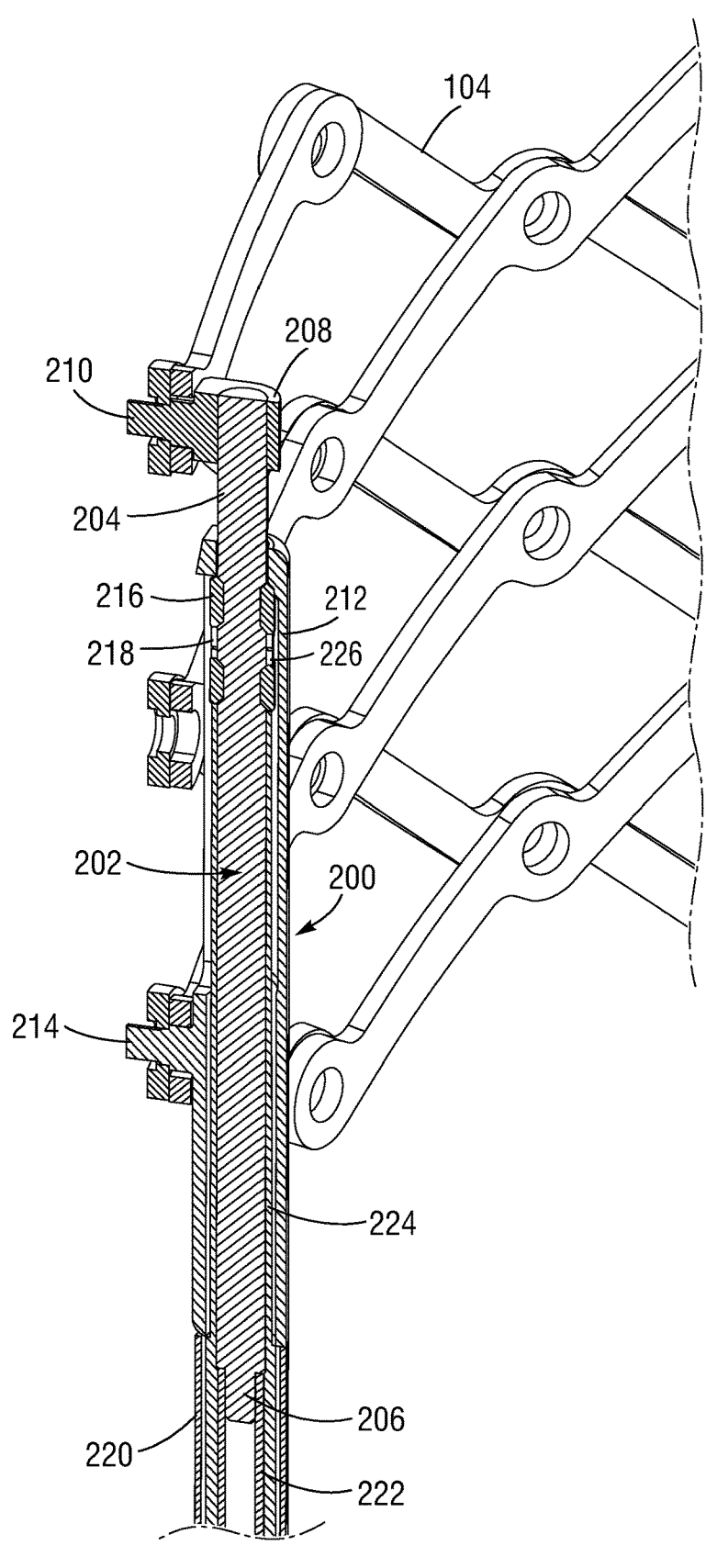

FIG. 6 is another perspective view of one of the expansion and locking mechanisms of FIG. 3, FIG. 7 shows a cross sectional view of one of the expansion and locking mechanisms of FIG. 3 along with a portion of the frame.

Figure 8:
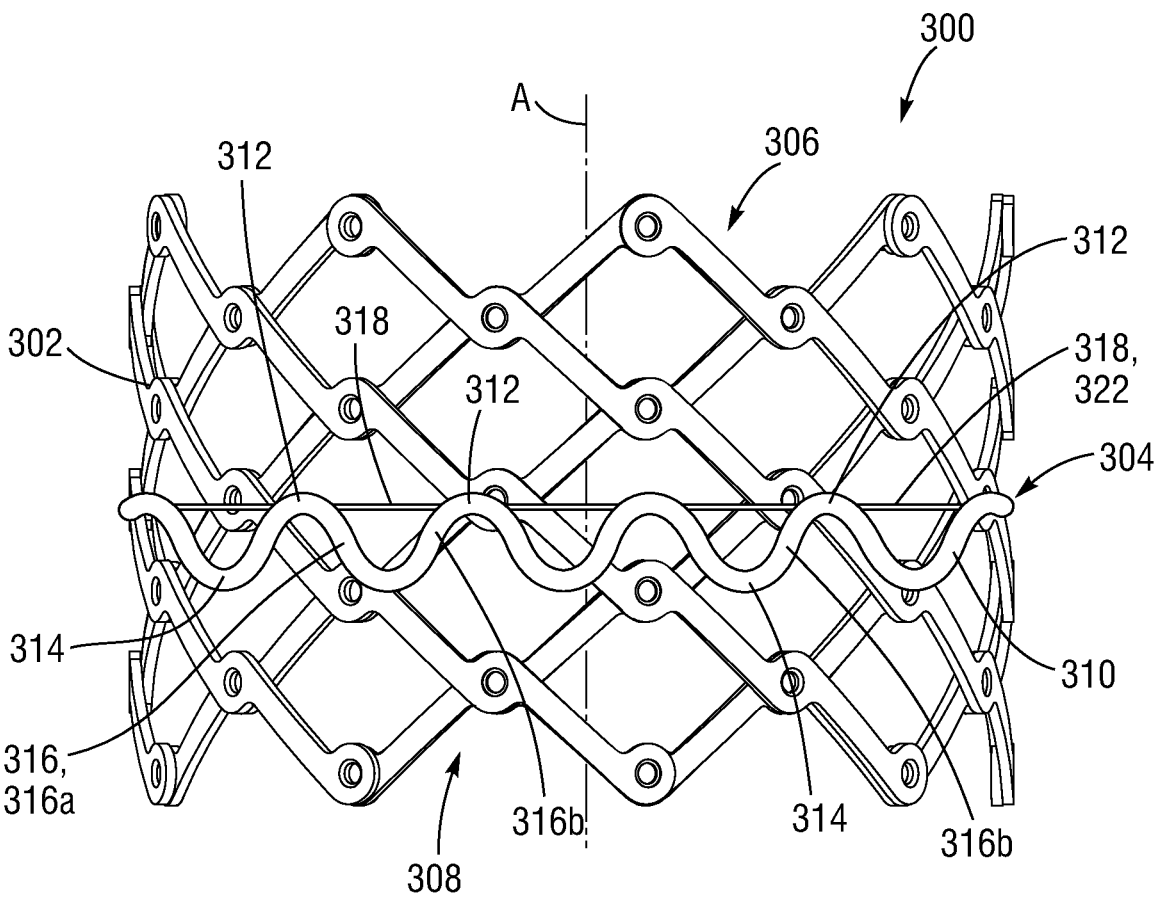

FIG. 8 is a side elevational view of a frame for a prosthetic heart valve including an exemplary embodiment of a valve belt shown in a radially expanded configuration.

Figure 9:
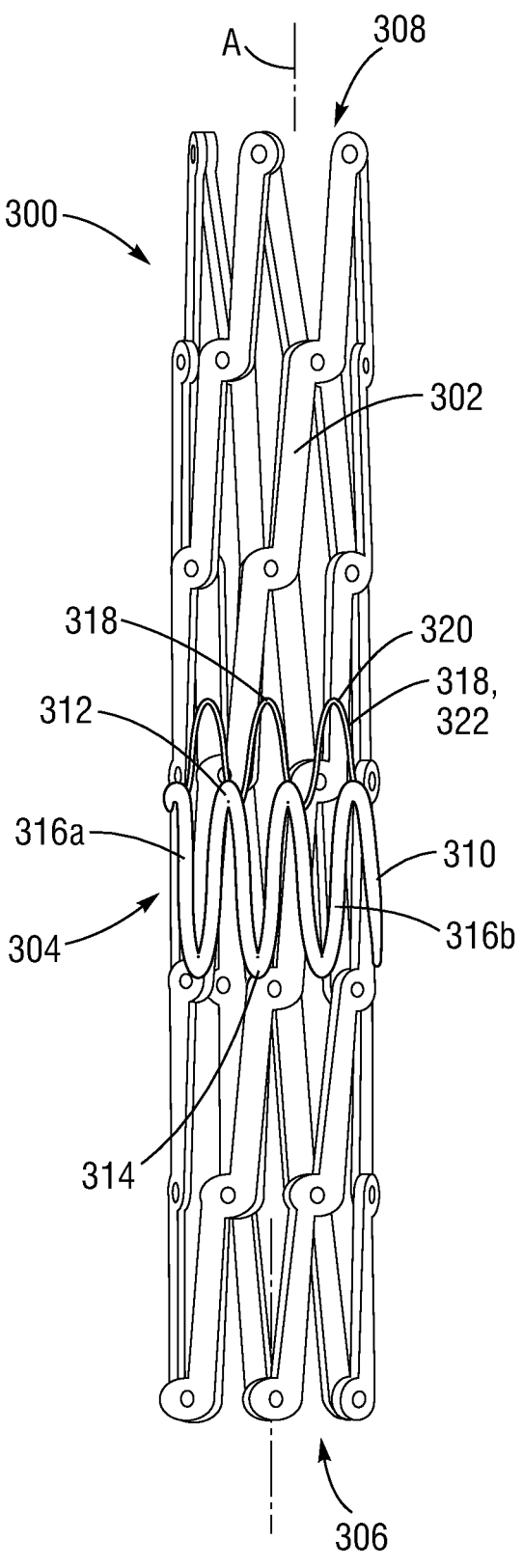

FIG. 9 is a side elevational view of the frame and belt of FIG. 8 shown in a radially compressed configuration.

Figure 10:
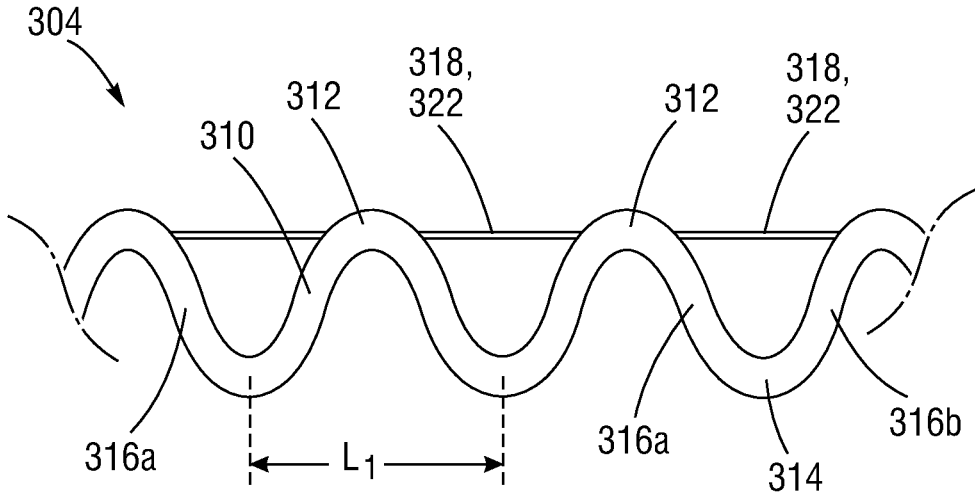

FIG. 10 is a side elevational view of a portion of the valve belt of FIG. 8 shown in a radially expanded configuration.

Figure 11:
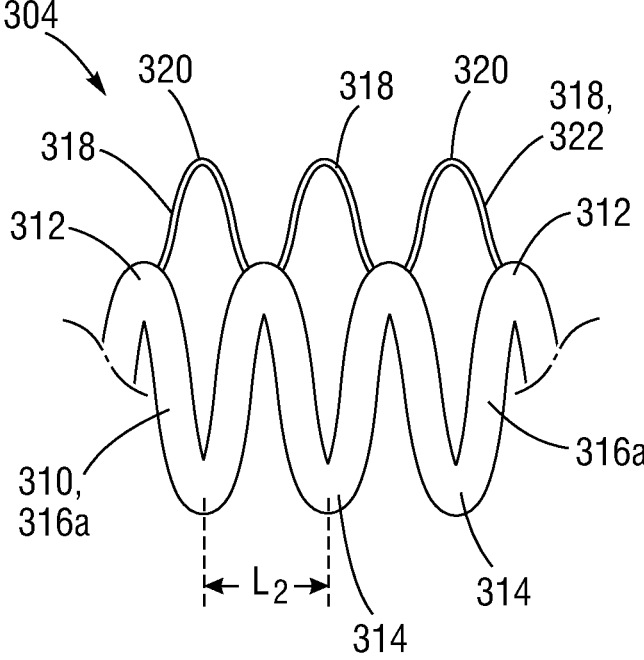

FIG. 11 is a side elevational view of a portion of the valve belt of FIG. 8 shown in a radially compressed configuration.

Figures 12, 13:
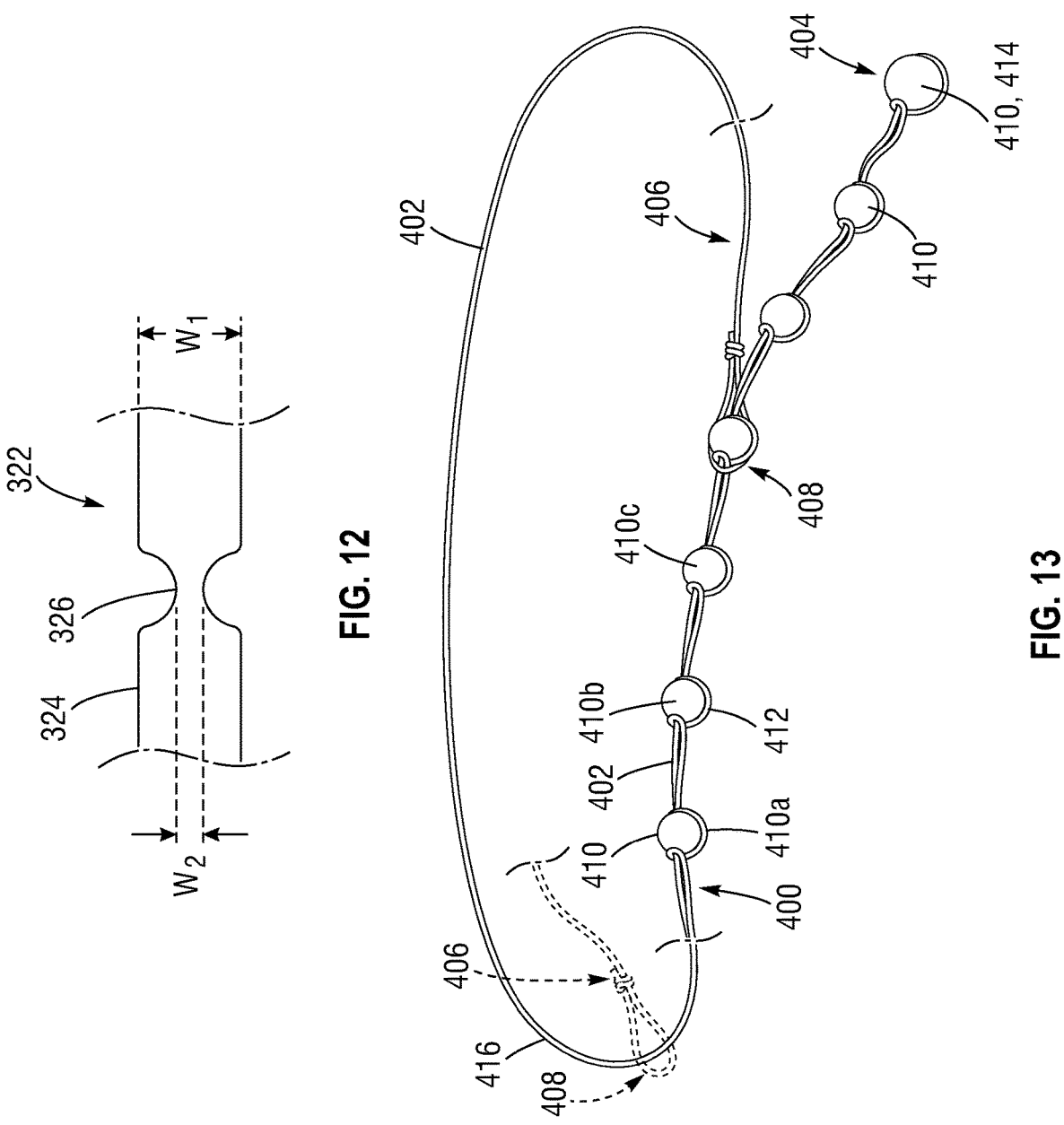

FIG. 12 is a side elevational view of a portion of an exemplary embodiment of a valve belt.

FIG. 13 is a perspective view of a portion of an exemplary embodiment of a valve belt.

Figure 14:
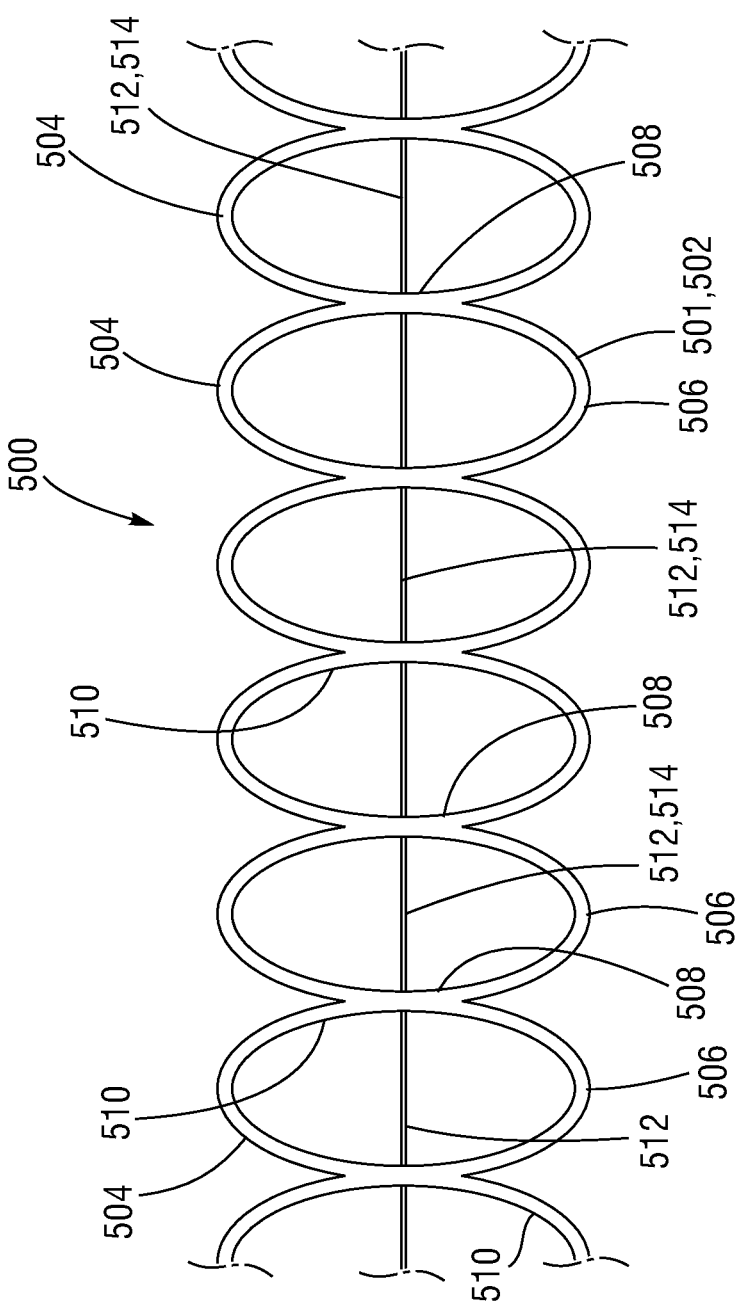

FIG. 14 is a side elevational view of a portion of an exemplary embodiment of a valve belt shown in a radially expanded configuration.

Figure 15:
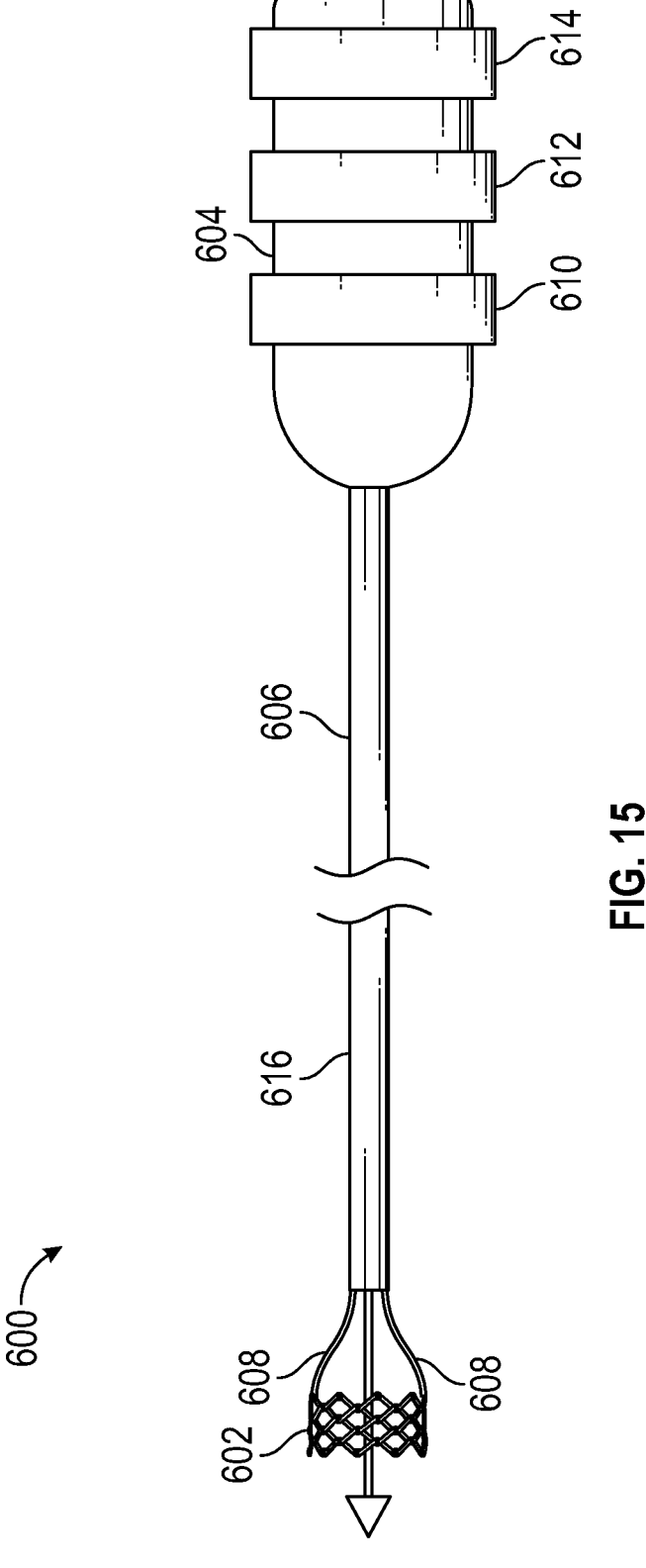

FIG. 15 is a side elevation view of a delivery apparatus for a prosthetic heart valve, according to one embodiment.

Figures 16, 17:
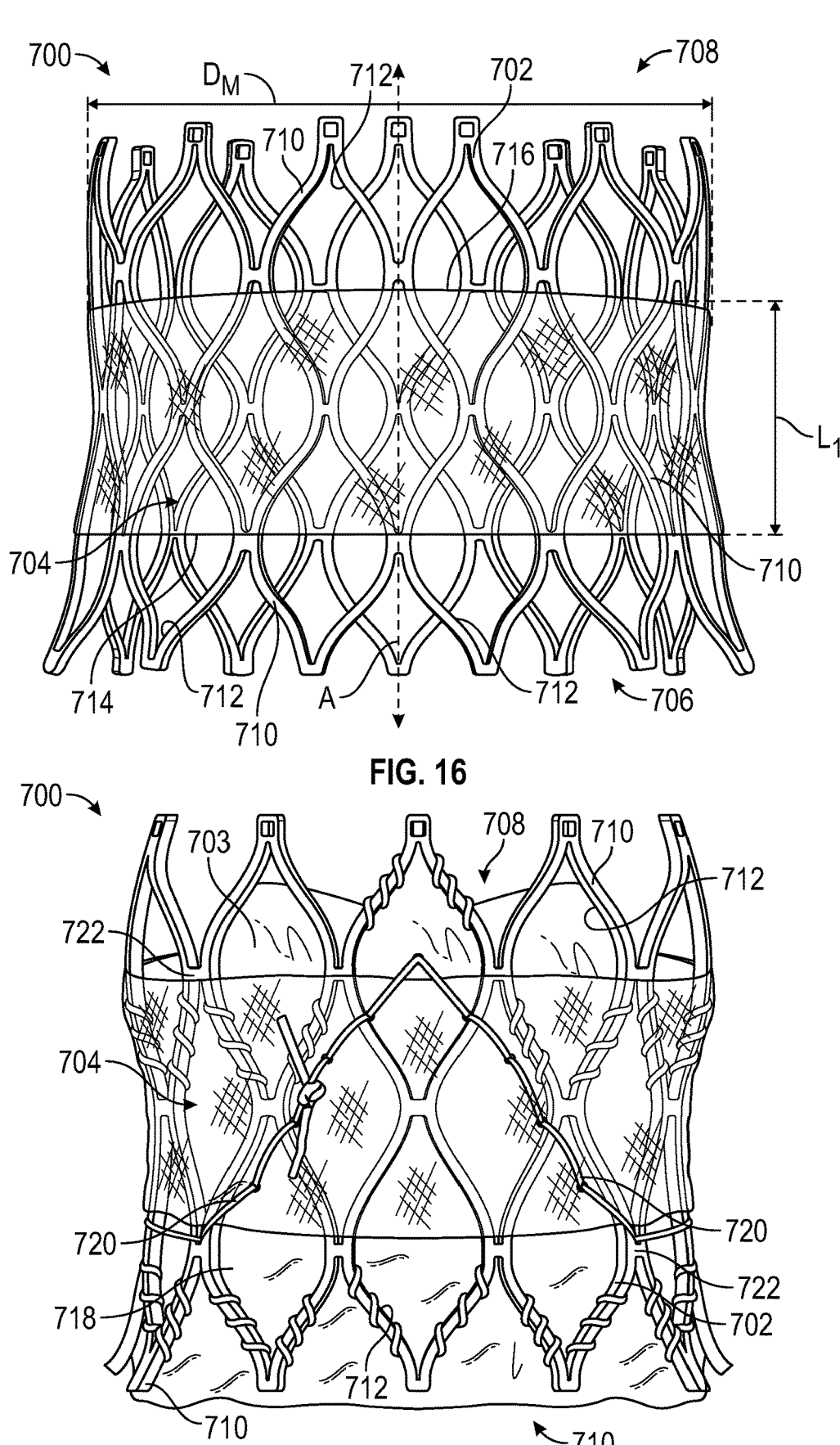

FIG. 16 is a perspective view of a frame for a prosthetic heart valve including an exemplary embodiment of a restriction band with the frame shown in a radially expanded configuration.

FIG. 17 is a perspective of a prosthetic heart valve comprising the frame and restriction band of FIG. 16.

Figure 18:
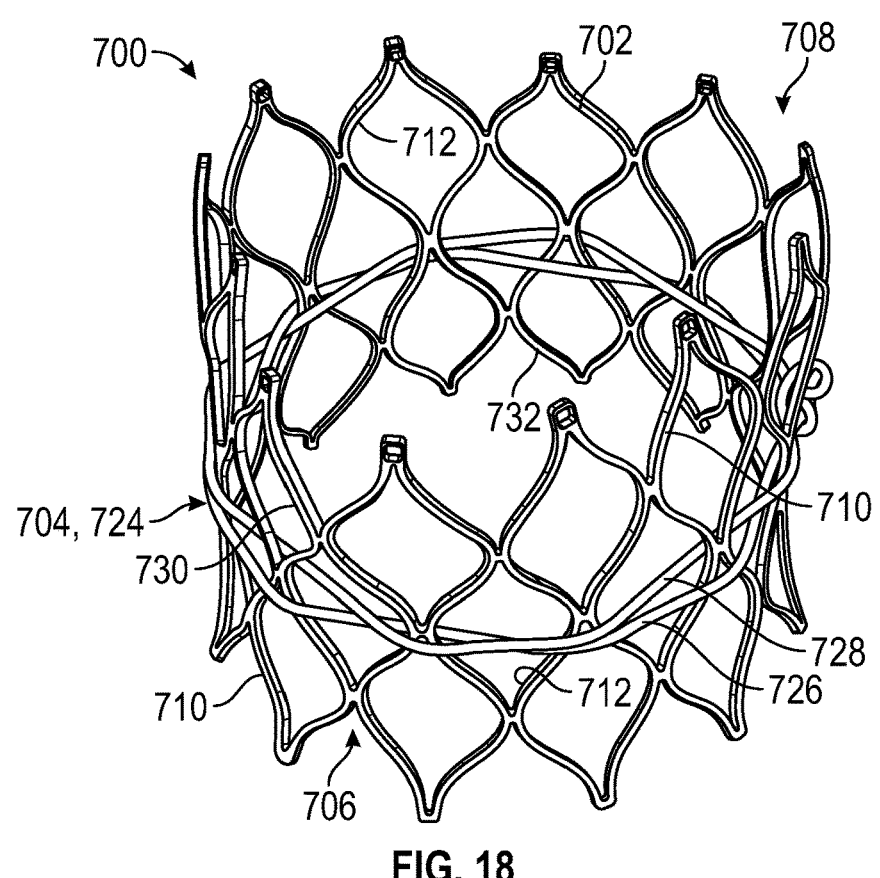

FIG. 18 is a perspective view of the frame of FIG. 16 including an exemplary embodiment of a restriction belt with the frame shown in a radially expanded configuration.

Figure 19:
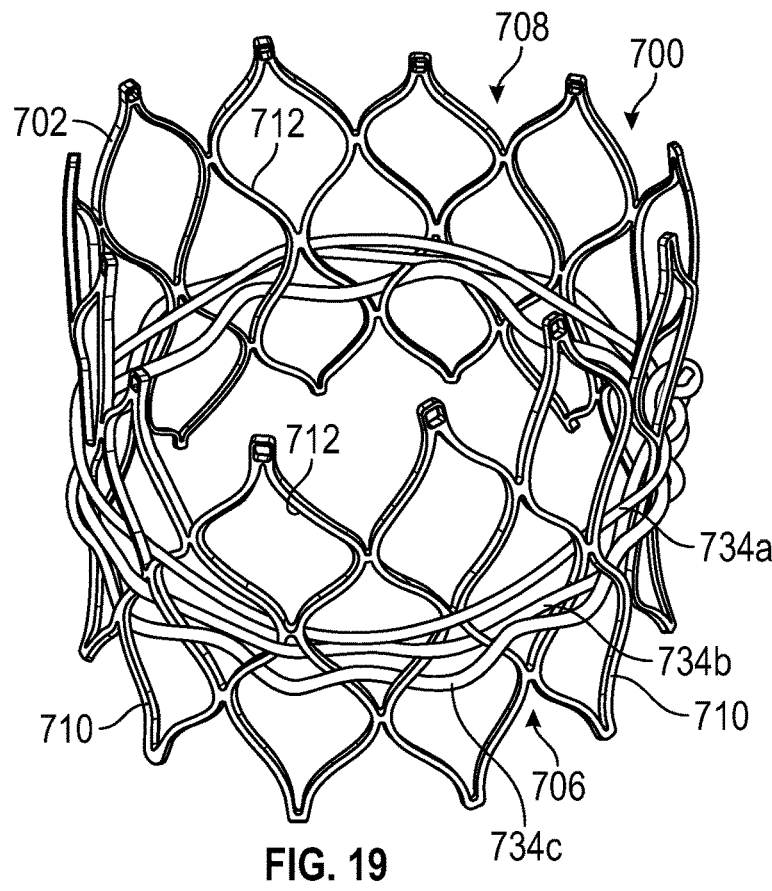

FIG. 19 is a perspective view of the frame of FIG. 16 including an exemplary embodiment of a plurality of restriction belts with the frame shown in a radially expanded configuration.

Figure 20:
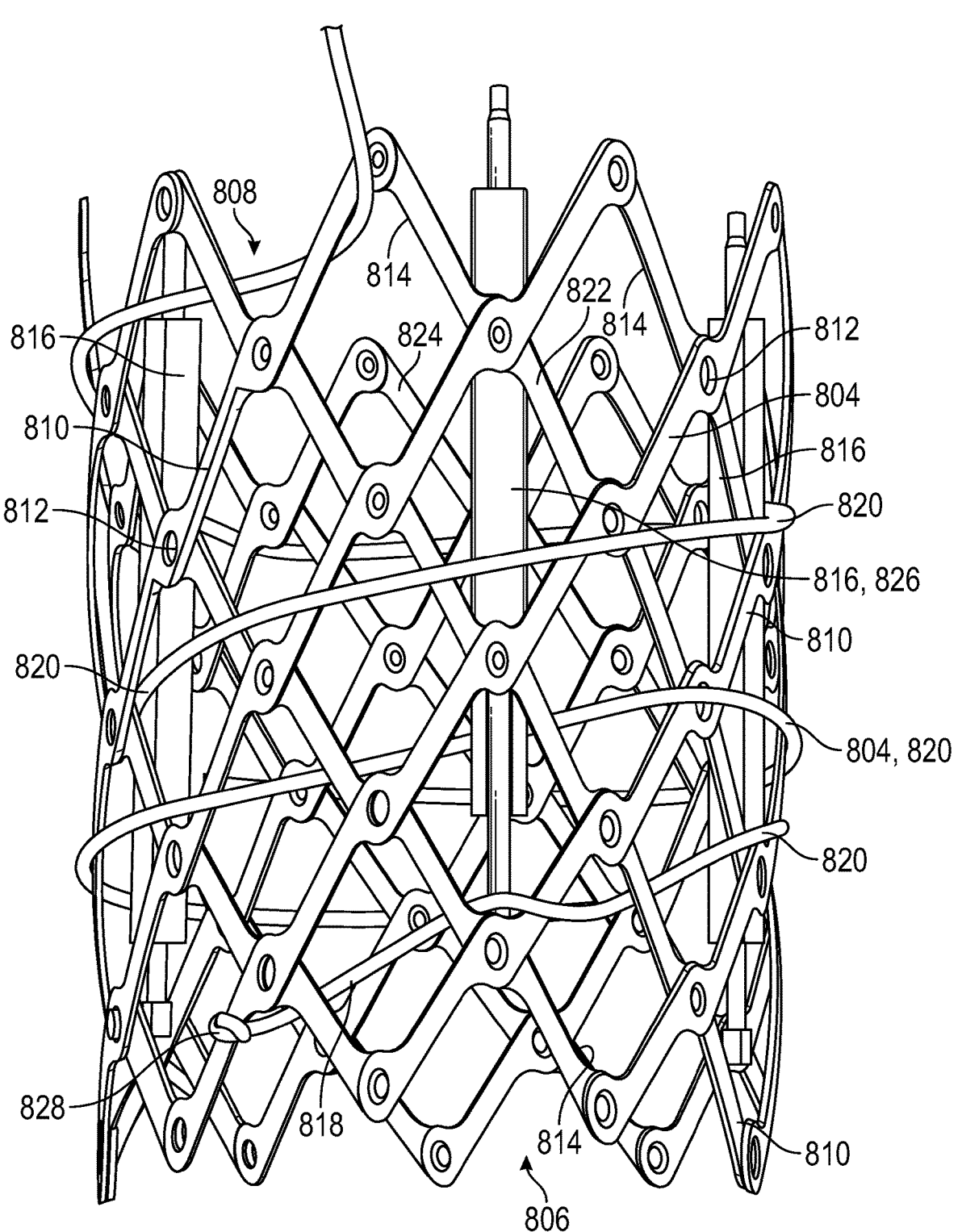

FIG. 20 is a perspective view of a frame for a prosthetic heart valve including an exemplary embodiment of a helical tension member with the frame shown in a partially radially expanded configuration.

Figure 21:
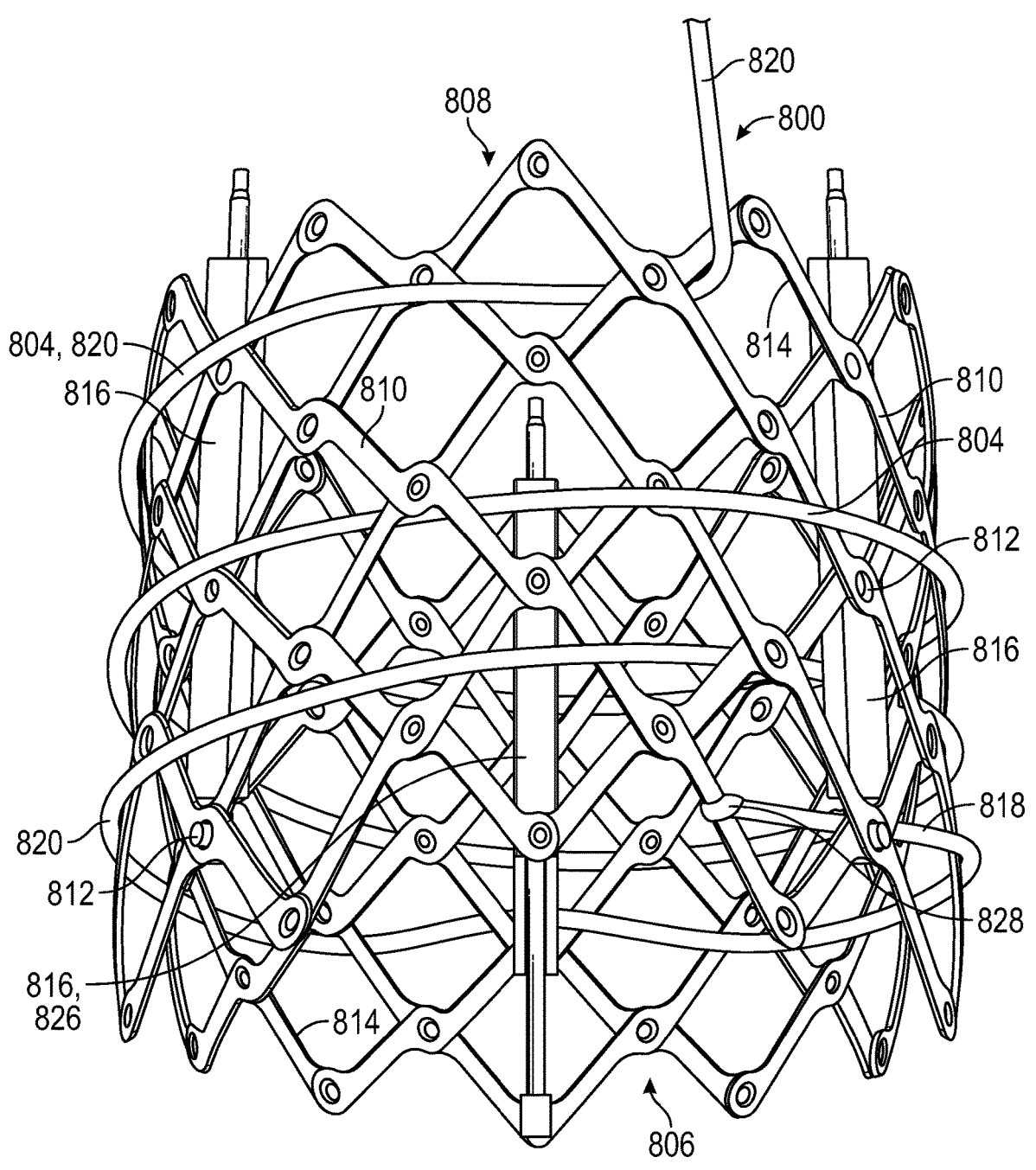

FIG. 21 is a perspective view of the frame and helical tension member of FIG. 20 with the frame shown in the radially expanded configuration.

DETAILED DESCRIPTION

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, a belt 304 as shown in FIGS. 10-11 can be used in combination with prosthetic valve 10. In another embodiment, a belt 400 as shown in FIG. 13 can be used in combination with the prosthetic valve 10 shown in FIG. 1.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Examples of the Disclosed Technology

Described herein are examples of prosthetic implant delivery assemblies and components thereof which can improve a physician's ability to control the size of a mechanically-expandable prosthetic implant, such as prosthetic valves (e.g., prosthetic heart valves or venous valves), stents, or grafts, as well as facilitate separation of the prosthetic implant from the delivery assembly, during the implantation procedure. The present disclosure also provides belts for use with such prosthetic implants. The belts can comprise frangible portions configured to break when a predetermined force is applied, thus allowing the force exerted by the prosthetic implant on the native anatomy to be calculated.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses, and examples thereof will be discussed in more detail later.

Figure 1:
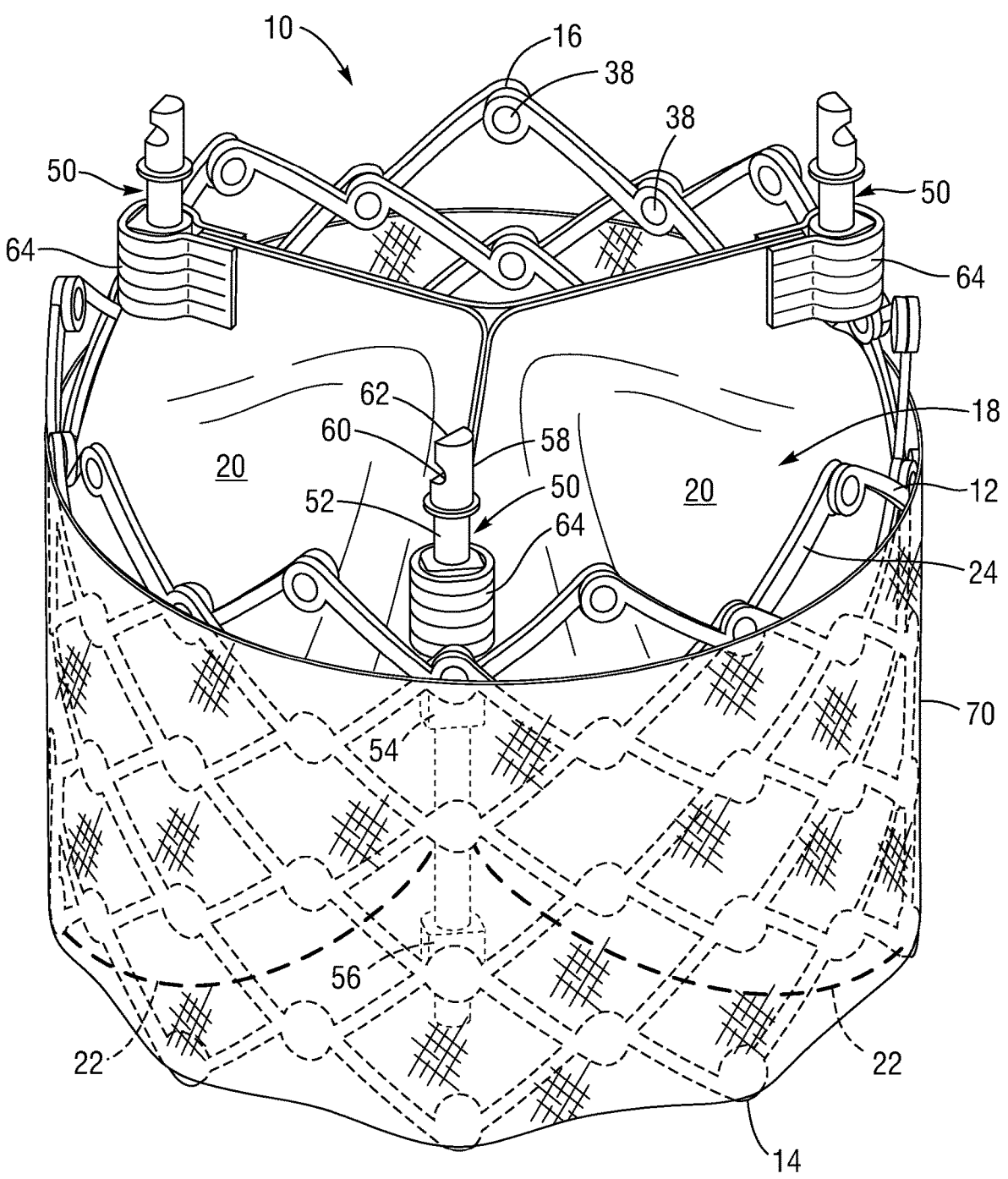
FIG. 1 is a perspective view of a prosthetic heart valve, according to one embodiment.

FIG. 1 shows an exemplary prosthetic valve 10, according to one embodiment. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 102.

In the depicted embodiment, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some embodiments, the inflow edge portions 22 of the leaflets 20 can be sutured to adjacent struts of the frame generally along the scallop line. In other embodiments, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Patent Publication No. 2018/0325665 and U.S. application Ser. No. 16/941,776, all of which are incorporated herein by reference in their entireties.

Figure 2A:
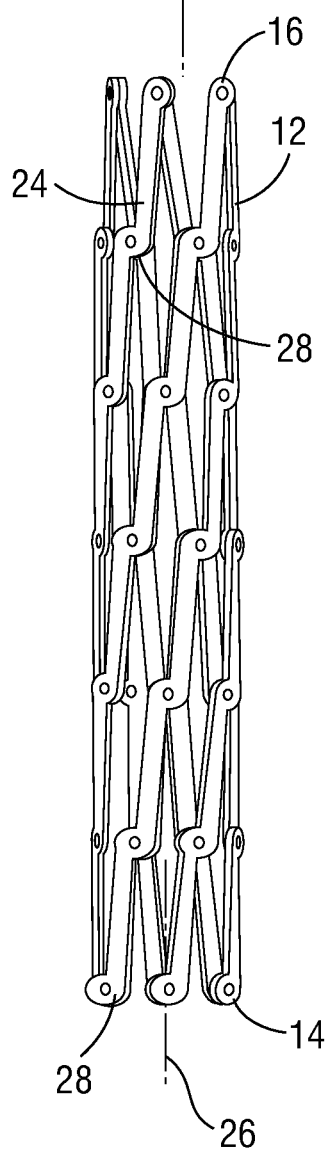
FIG. 2A is a side elevation view of the frame of the prosthetic heart valve of FIG. 1, shown in a radially compressed state.
Figure 2B:
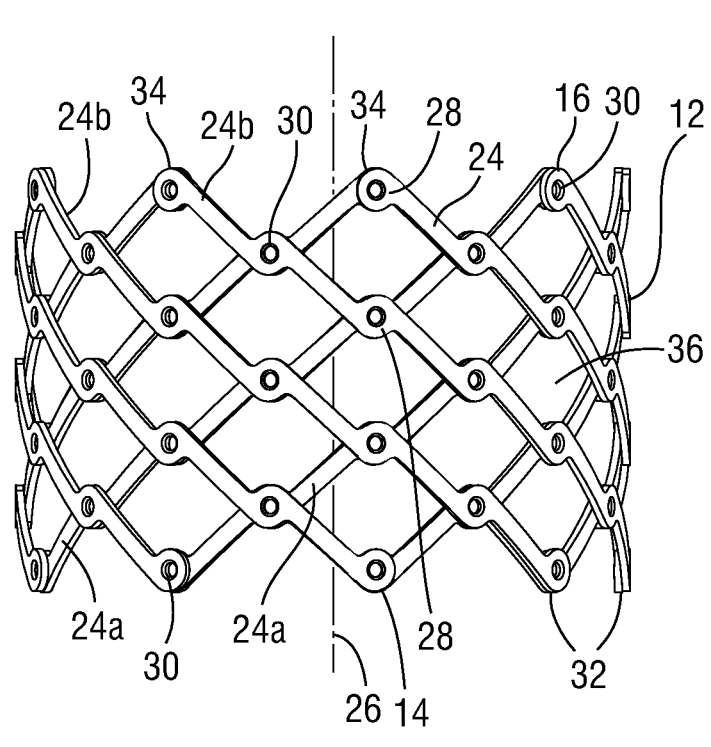
FIG. 2B is a side elevation view of the frame of the prosthetic heart valve of FIG. 1, shown in a radially expanded state.

The prosthetic valve 10 can be radially compressible and expandable between a radially compressed configuration and a radially expanded configuration. FIGS. 2A-2B show the bare frame 12 of the prosthetic valve 10 (without the leaflets and other components) for purposes of illustrating expansion of the prosthetic valve 10 from the radially compressed configuration (FIG. 2A) to the radially expanded configuration (FIG. 2B).

The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10. In FIG. 2B, the struts 24 are shown as positioned diagonally, or offset at an angle relative to, and radially offset from, a longitudinal axis 26 of the prosthetic valve 10 when the prosthetic valve 10 is in the expanded configuration. In other implementations, the struts 24 can be offset by a different amount than depicted in FIG. 2B, or some or all of the struts 24 can be positioned parallel to the longitudinal axis 26 of the prosthetic valve 10.

The struts 24 can comprise a set of inner struts 24a (extending from the lower left to the upper right of the frame in FIG. 2B) and a set of outer struts 24b (extending from the upper left to the lower right of the frame in FIG. 2B) connected to the inner struts 24a. The open lattice structure of the frame 12 can define a plurality of open frame cells 36 between the struts 24.

The struts 24 can be pivotably coupled to one another at one or more pivot joints or pivot junctions 28 along the length of each strut. For example, in one embodiment, each of the struts 24 can be formed with apertures 30 at opposing ends of the strut and apertures spaced along the length of the strut. Respective hinges can be formed at the locations where struts 24 overlap each other via fasteners 38 (FIG. 1), such as rivets or pins that extend through the apertures 30. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some embodiments, the frame 12 can be constructed by forming individual components (e.g., the struts and fasteners of the frame) and then mechanically assembling and connecting the individual components together. Further details regarding the construction of the frame and the prosthetic valve are described in U.S. Pat. No. 10,603,165, U.S. Publication Nos. 2018/0344456 and 2019/0060057, and U.S. patent application Ser. No. 16/941,776, all of which are incorporated herein by reference.

In the illustrated embodiment, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated embodiment, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other embodiments, the actuators 50 can be reciprocating type actuators configured to apply axial directed forces to the frame to produce radial expansion and compression of the frame. For example, the rod 52 of each actuator can be fixed axially relative to the nut 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated embodiments, the prosthetic valve 10 includes three such actuators 50, although a greater or fewer number of actuators could be used in other embodiments. The leaflets 20 can have commissure attachments members 64 that wrap around the sleeves 54 of the actuators 50. Further details of the actuators, locking mechanisms and delivery apparatuses for actuating the actuators can be found in U.S. Pat. No. 10,603,165 and U.S. Patent Publication Nos. 2019/0060057, 2018/0153689, and 2018/0325665, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some embodiments, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paraval-vular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. patent application Ser. No. 16/941,776, which is incorporated herein by reference in its entirety.

FIGS. 3-4 show another embodiment of a prosthetic valve 100 comprising a frame 104 and expansion and locking mechanisms 200 (also referred to as "actuators"). It should be understood that the prosthetic valve 100 can include leaflets 20 and other soft components, such as one or more skirts 70, which are removed for purposes of illustration. Expansion and locking mechanism 200 can be used to both radially expand and lock the prosthetic valve in a radially expanded state. In the example of FIGS. 3 and 4, three expansion and locking mechanisms 200 are attached to the frame 104 but in other example delivery assemblies, any number of expansion and locking mechanisms 200 can be used. FIG. 3 shows the expansion and locking mechanisms 200 attached to the frame 104 when the frame is in a radially collapsed configuration and FIG. 4 shows expansion and locking mechanisms attached to the frame when the frame is in a radially expanded configuration.

It will be appreciated that prosthetic valve 100 can, in certain embodiments, use other mechanisms for expansion and locking, such as linear actuators, alternate locking mechanisms, and alternate expansion and locking mechanisms. Further details regarding the use of linear actuators, locking mechanisms, and expansion and locking mechanisms in prosthetic valve can be found, for example, in U.S. Pat. No. 10,603,165, which is incorporated herein by reference in its entirety.

Referring to FIGS. 5A-5C, the expansion and locking mechanism 200 in the illustrated embodiment can include an actuator screw 202 (which functions as a linear actuator or a push-pull member in the illustrated embodiment) comprising a relatively long upper, or distal, portion 204 and a relatively shorter lower, or proximal, portion 206 at the proximal end of the screw 200, wherein the lower portion has a smaller diameter than the upper portion. Both the upper and lower portions 204, 206 of the screw 202 can have externally threaded surfaces.

The actuator screw 200 can have a distal attachment piece 208 attached to its distal end having a radially extending distal valve connector 210. The distal attachment piece 208 can be fixed to the screw 202 (e.g., welded together or manufactured as one piece). The distal valve connector 210 can extend through an opening at or near the distal end of the frame 104 formed at a location on the frame where two or more struts intersect as shown in FIG. 5C. The distal valve connector 210 can be fixed to the frame 104 (e.g., welded). Due to the shape of the struts, the distal end of the frame 104 comprises an alternating series of distal junctions 150 and distal apices 152. In the illustrated example, the distal valve connectors 210 of the three expansion and locking mechanisms 200 are connected to the frame 104 through distal junctions 150. In other examples, one or more distal valve connectors 210 can be connected to the frame 104 through distal apices 152. In other embodiments, the distal valve connectors 210 can be connected to junctions closer to the proximal end of the frame 104.

The expansion and locking mechanism 200 can further include a sleeve 212. The sleeve 212 can be positioned annularly around the distal portion 204 of the screw 202 and can contain axial openings at its proximal and distal ends through which the screw 202 can extend. The axial openings and the lumen in the sleeve 212 can have a diameter larger than the diameter of the distal portion 204 of the screw 202 such that the screw can move freely within the sleeve (the screw 202 can be moved proximally and distally relative to the sleeve 212). Because the actuator screw 202 can move freely within the sleeve, it can be used to radially expand and/or contract the frame 104 as disclosed in further detail below.

The sleeve 212 can have a proximal valve connector 214 extending radially from its outer surface. The proximal valve connector 214 can be fixed to the sleeve 212 (e.g., welded). The proximal valve connector 214 can be axially spaced from the distal valve connector 210 such that the proximal valve connector can extend through an opening at or near the proximal end of the frame 104. The proximal end of the frame 104 comprises an alternating series of proximal junctions 160 and proximal apices 162. In the illustrated example, the proximal valve connectors 214 of the three expansion and locking mechanisms 200 are connected to the frame 104 through proximal junctions 160. In other examples, one or more proximal valve connectors 214 can be connected to the frame 104 through proximal apices 162. In other embodiments, the proximal valve connectors 214 can be connected to junctions closer to the distal end of the frame 104.

It should be understood that the distal and proximal connectors 210, 214 need not be connected to opposite ends of the frame. The actuator 200 can be used to expand and compress the frame as long as the distal and proximal connectors are connected to respective junctions on the frame that are axially spaced from each other.

A locking nut 216 can be positioned inside of the sleeve 212 and can have an internally threaded surface that can engage the externally threaded surface of the actuator screw 202. The locking nut 216 can have a notched portion 218 at its proximal end, the purpose of which is described below. The locking nut can be used to lock the frame 104 into a particularly radially expanded state, as discussed below.

FIGS. 6 and 7 shows the expansion and locking mechanism 200 including components of a delivery apparatus not shown in FIGS. 5A-5C. As shown, the expansion and locking mechanism 200 can be releasably coupled to a support tube 220, an actuator member 222, and a locking tool 224. The proximal end of the support tube 220 can be connected to a handle or other control device (not shown) that a doctor or operator of the delivery assembly utilizes to operate the expansion and locking mechanism 200 as described herein. Similarly, the proximal ends of the actuator member 222 and the locking tool 224 can be connected to the handle.

The support tube 220 annularly surrounds a proximal portion of the locking tool 224 such that the locking tool extends through a lumen of the support tube. The support tube 220 and the sleeve are sized such that the distal end of the support tube abuts or engages the proximal end of the sleeve 212 such that the support tube is prevented from moving distally beyond the sleeve.

The actuator member 222 extends through a lumen of the locking tool 224. The actuator member 222 can be, for example, a shaft, a rod, a cable, or wire. The distal end portion of the actuator member 222 can be releasably connected to the proximal end portion 206 of the actuator screw 202. For example, the distal end portion of the actuator member 222 can have an internally threaded surface that can engage the external threads of the proximal end portion 206 of the actuator screw 202. Alternatively, the actuator member 222 can have external threads that engage an internally threaded portion of the screw 202. When the actuator member 222 is threaded onto the actuator screw 202, axial movement of the actuator member causes axial movement of the screw.

The distal portion of the locking tool 224 annularly surrounds the actuator screw 202 and extends through a lumen of the sleeve 212 and the proximal portion of the locking tool annularly surrounds the actuator member 222 and extends through a lumen of the support tube 220 to the handle of the delivery device. The locking tool 224 can have an internally threaded surface that can engage the externally threaded surface of the locking screw 202 such that clockwise or counter-clockwise rotation of the locking tool 224 causes the locking tool to advance distally or proximally along the screw, respectively.

The distal end of the locking tool 224 can comprise a notched portion 226, as can best be seen in FIG. 6. The notched portion 226 of the locking tool 224 can have an engagement surface 227 that is configured to engage a correspondingly shaped engagement surface 219 of the notched portion 218 of the locking nut 216 such that rotation of the locking tool (e.g., clockwise rotation) causes the nut 216 to rotate in the same direction (e.g., clockwise) and advance distally along the locking screw 202. The notched portions 218, 226 in the illustrated embodiment are configured such that rotation of the locking tool 224 in the opposite direction (e.g., counter-clockwise) allows the notched portion 226 of the tool 224 to disengage the notched portion 218 of the locking nut 216; that is, rotation of the locking tool in a direction that causes the locking tool to move proximally does not cause corresponding rotation of the nut.

In alternative embodiments, the distal end portion of the locking tool 224 can have various other configurations adapted to engage the nut 216 and produce rotation of the nut upon rotation of the locking tool for moving the nut distally, such as any of the tool configurations described herein. In some embodiments, the distal end portion of the locking tool 224 can be adapted to produce rotation of the nut 216 in both directions so as move the nut distally and proximally along the locking screw 202.

In operation, prior to implantation, the actuator member 222 is screwed onto the proximal end portion 206 of the actuator screw 202 and the locking nut 216 is rotated such that it is positioned at the proximal end of the screw. The frame 104 can then be placed in a radially collapsed state and the delivery assembly can be inserted into a patient. Once the prosthetic valve is at a desired implantation site, the frame 104 can be radially expanded as described herein.

To radially expand the frame 104, the support tube 220 is held firmly against the sleeve 212. The actuator member 222 is then pulled in a proximal direction through the support tube, such as by pulling on the proximal end of the actuator member or actuating a control knob on the handle that produces proximal movement of the actuator member. Because the support tube 220 is being held against the sleeve 212, which is connected to a proximal end of the frame 104 by the proximal valve connector 214, the proximal end of the frame is prevented from moving relative to the support tube. As such, movement of the actuator member 222 in a proximal direction causes movement of the actuator screw

202 in a proximal direction (because the actuator member is threaded onto the screw), thereby causing the frame 104 to foreshorten axially and expand radially. Alternatively, the frame 104 can be expanded by moving the support tube 220 distally while holding the actuator member 222 stationary or moving the support tube distally while moving the actuator member 222 proximally.

After the frame 104 is expanded to a desired radially expanded size, the frame can be locked at this radially expanded size as described herein. Locking the frame can be achieved by rotating the locking tool 224 in a clockwise direction causing the notched portion 226 of the locking tool to engage the notched portion 218 of the locking nut 216, thereby advancing the locking nut distally along the actuator screw 202. The locking tool 224 can be so rotated until the locking nut 216 abuts an internal shoulder at the distal end of the sleeve 212 and the locking nut 216 cannot advance distally any further (see FIG. 6). This will prevent the screw 202 from advancing distally relative to the sleeve 212 and radially compressing the frame 104. However, in the illustrated embodiment, the nut 216 and the screw 202 can still move proximally through the sleeve 212, thereby allowing additional expansion of the frame 104 either during implantation or later during a valve-in-valve procedure.

Once the frame 104 is locked in radially expanded state, the locking tool 224 can be rotated in a direction to move the locking tool proximally (e.g., in a counter-clockwise direction) to decouple the notched portion 226 from the notched portion 218 of the locking nut 216 and to unscrew the locking tool from the actuator screw 202. Additionally, the actuator member 222 can be rotated in a direction to unscrew the actuator member from the lower portion 206 of the actuator screw 202 (e.g., the actuator member 222 can be configured to disengage from the actuator screw when rotated counter-clockwise). Once the locking tool 224 and the actuator member 222 are unscrewed from the actuator screw 202, they can be removed from the patient along with the support tube 220, leaving the actuator screw and the sleeve 212 connected to the frame 104, as shown in FIG. 5C, with the frame 104 locked in a particular radially-expanded state.

In an alternative embodiment, the locking tool 224 can be formed without internal threads that engage the external threads of the actuator screw 202, which can allow the locking tool 224 to be slid distally and proximally through the sleeve 212 and along the actuator screw 202 to engage and disengage the nut 216.

In some embodiments, additional designs for expansion and locking mechanisms can be used instead of the design previously described. Details on expansion and locking mechanisms can be found, for example, in U.S. Pat. No. 10,603,165, which is incorporated herein by reference in its entirety.

FIGS. 8-9 illustrate another exemplary embodiment of a prosthetic heart valve 300 comprising a frame 302 and further including a belt 304 configured as a force measurement device. The prosthetic valve 300 can have an outflow end portion 306 and an inflow end portion 308 and can include a valvular structure (e.g., valvular structure 18) and inner and/or outer skirts, as previously described, although these components are omitted for purposes of illustration. The prosthetic valve 300 can also have actuators and/or locking mechanisms as previously described. While only one side of the frame 302 is depicted in FIGS. 8-9, it should be appreciated that frame 302 forms an annular structure similar to frame 12 of prosthetic valve 10 described previously, and that belt 304 has an annular shape extending around the frame 302.

The valve belts herein are described with reference to mechanically-expandable valves, such as the valves described in U.S. Pat. No. 10,603,165 and U.S. Provisional Application No. 63/085,947, filed Sep. 30, 2020, each of which is incorporated herein by reference. For example, some mechanical valves can comprise pivotable junctions between the struts, while others can comprise a unitary lattice frame expandable and/or compressible via mechanical means. However, it should be appreciated that the valve belts can additionally be used with other types of transcatheter prosthetic valves, including balloon-expandable prosthetic heart valves, such as disclosed in U.S. Pat. No. 9,393,110, and U.S. Publication Nos. U.S. 2018/0028310 and 2019/0365530, each of which are incorporated herein by reference, and self-expandable prosthetic heart valves, such as disclosed in U.S. Pat. No. 10,098,734, which is incorporated herein by reference.

One or more selected portions of the belt 304 can be configured to rupture or break when a predetermined amount force (e.g., radial force) is applied to the belt 304 by the prosthetic valve 300, as described in more detail below. In this way, the belt 304 can be used to determine the real-time diameter of the prosthetic valve and thereby calculate the radial force applied by the prosthetic valve 300 against the surrounding tissue (e.g., the native annulus). When implanting a mechanically expandable prosthetic valve (e.g., prosthetic valve 300) it is desirable to expand the prosthetic valve to the maximum size allowed by the patient's anatomical considerations while mitigating the risk of annular rupture (e.g., by selecting a size similar to the native annulus). To ensure optimal implantation size, the diameter of the prosthetic valve and the radial force applied to the annulus by the prosthetic valve can be monitored in real time during the implantation process using a measurement device such as belt 304.

The belt 304 can comprise a generally annular or toroidal body 310 extending around the circumference of the frame 302. The body 310 can have a continuous, undulating shape comprising a plurality of peaks 312 alternating with a plurality of valleys 314 around its circumference. The peaks 312 can be positioned such that they are above the valleys 314 along a longitudinal axis A of the prosthetic valve in the orientation shown in FIG. 8. In the illustrated embodiment, the peaks 312 point toward the outflow end 306 of the prosthetic valve 300 and the valleys 314 point toward the inflow end 308 of the prosthetic valve 300.

A plurality of struts 316 can connect adjacent peaks and/or valleys 312, 314. For example, in the illustrated embodiment, from left to right, a first strut 316a extends from each peak 312 to each valley 314 and a second strut 316b extend up from the valley to the next peak 312. The struts 316 can be configured in a variety of shapes and sizes, e.g., straight, curved, zig-zag, symmetrical, asymmetrical, etc. For example, in the illustrated embodiment each strut has a curved shape.

In an alternative embodiment, the annular body 310 of the belt can be formed of strut sections coupled to one another at respective hinges where the strut sections overlap. For example, the strut sections can overlap at each peak 312 and/or valley 314 and can be coupled together via fasteners, such as rivets or pins that extend through the strut sections. The hinges can allow the strut sections to pivot relative to one another as the belt 304 is radially expanded or compressed, such as during expansion and/or compression of the prosthetic valve 300.

As shown in the illustrated embodiment, the body 310 can be radially compressible and expandable between a radially compressed state (FIGS. 9 and 11) and a radially expanded state (FIGS. 8 and 10). Thus, the belt 304 can be crimped or retained on the radially compressed prosthetic valve in the radially compressed state during delivery, and then expanded to the radially expanded state by expansion of the prosthetic valve at the implantation site.

As shown in FIGS. 10-11, when the belt 304 is in the radially expanded position, the circumferential length between adjacent peaks 312 and/or adjacent valleys 314 can be greater than the circumferential length between adjacent peaks 312 and/or adjacent valleys 314 when in the radially compressed state. For example, in FIG. 10 the adjacent valleys 314 have a first circumferential length $L_1$ between them, and in FIG. 11 the adjacent valleys have a second, smaller circumferential length $L_2$ between them.

In particular embodiments, the belt 304 (including the body 310, and extension members 318 and/or frangible members 322, described below) can be made of any of the materials described above for the frame 12, including, but not limited to, any of various plastically expandable materials (e.g., stainless steel or a cobalt-chromium alloy) or self-expandable materials (e.g., Nitinol).

In some embodiments, the belt 304 (including the body 310, and extension members 318 and/or frangible members 322) can be made of a bioresorbable material. In such embodiments, after the prosthetic valve 300 has been implanted at a selected implantation site within a patient's body, the belt 304 may dissolve and/or be absorbed by the patient's body. For example, in some embodiments the belt 304 can comprise a bioresorbable polymer configured to dissolve over time. The resorption rate of the bioresorbable belt 304 can be controlled using a variety of parameters including the polymer material, additives, processing, etc. Exemplary bioresorbable materials include, but are not limited to, Polylactide (PLA), Poly-L-Lactide (PLLA), Polyglycolide (PGA), Poly-e-Caprolactone (PCL), Trimethylene carbonate (TMC), Poly-DL-Lactide (PDLLA), Poly-b-hydroxybutyrate (PBA), Poly-p-dioxanone (PDO), Poly-b-hydroxyproprionate (PHPA), and Poly-b-malic acid (PMLA). In other embodiments, the body 310 can be formed from a suitable super-elastic metal or alloy, such as Nitinol. Optionally, spring steel, a cobalt-chrome alloy such as Elgiloy®, or other such elastic metals can be utilized.

The belt 304 can further comprise a plurality of circumferentially-extending extension members 318 extending between adjacent portions of the body 310. For example, in the illustrated embodiment, the extension members 318 extend between one or more adjacent peaks 312. However, in other embodiments, the extension members 318 can extend between adjacent valleys 314. In still other embodiments, some extension members 318 can extend between adjacent peaks 312 and other extension members 318 can extend between adjacent valleys 314.

In some embodiments, each pair of adjacent peaks 312 and/or adjacent valleys 314 can comprise an extension member 318 between them. For example, in the illustrated embodiment, each pair of adjacent peaks comprises an extension member 318. However, in other embodiments, only selected pairs of adjacent peaks 312 and/or selected pairs of adjacent valleys 314 can comprise an extension member between them.

As shown in FIG. 10, when the belt 304 is in the radially expanded condition, the extension members 318 can extend substantially parallel to the circumference of the frame 302. When the belt 304 is in the radially compressed configuration, as shown in FIG. 11, the extension members 318 can deform axially toward the inflow and/or outflow end portions 306, 308 of the frame 302. In the illustrated embodiment, as shown in FIG. 9, the extension members 318 deform axially toward the outflow end portion 308 of the frame 302, forming a substantially U- or V-shaped member having an apex 320.

One or more selected extension members 318 can be configured as frangible members 322. The one or more frangible members 322 can be configured to break, rupture, or otherwise deform when a force (e.g., a radial force) greater than a predetermined threshold of force is applied to the belt 304, for example, by the frame 302.

As the frame 302 moves from the radially compressed configuration (FIG. 9) to the radially expanded configuration (FIG. 10), the frame foreshortens axially and expands radially. The belt 304 expands radially with the frame from a compressed diameter until it reaches a first predetermined diameter. As the prosthetic valve 300 continues to expand (e.g., using actuators 50) the frame 302 applies an increasingly greater radial force to the belt 304. When the force exceeds a first predetermined threshold, a first frangible member 322 can break, allowing the belt 304 to radially expand to a second predetermined diameter.

The radial force exerted by the prosthetic valve 300 on the native annulus when the belt 304 is at a particular diameter can be determined based at least in part on the known mathematical relationship between the prosthetic valve's diameter and the radial force the prosthetic valve exerts. During the implantation procedure, a physician can monitor the diameter of the valve to determine when the prosthetic valve is at the diameter that best fits the native annulus and when the optimal amount of radial force is being applied by the prosthetic valve to the native annulus.

As the actuators (e.g., actuators 50) continue to expand the prosthetic valve 300, the prosthetic valve 300 continues to apply force to the belt 304, which is now expanded to the second predetermined diameter. When the force exceeds a second predetermined threshold (which can be greater than or equal to the first predetermined threshold) a second frangible member 322 can break, allowing the body 310 to radially expand to a third predetermined diameter. Each time a frangible member 322 breaks, the diameter of the belt 304 (and therefore the diameter to which the frame 302 can expand) increases. The process of expansion and breakage can continue until the prosthetic valve has reached a selected size.

The belt 304 can comprise any number of frangible members 322. For example, in some embodiments, all the extension members 318 are frangible members 322. In other embodiments, only selected extension members 318 are frangible members 322.

In some embodiments, each frangible member 322 can be configured to break when the same predetermined threshold of force is exceeded. In other embodiments, each frangible member 322 can be configured to break when a different predetermined threshold of force is exceeded. In still other embodiments, a first set of frangible members 322 can be configured to break when a first predetermined threshold of force is exceeded, and a second set of frangible members 322 can be configured to break when a second predetermined threshold of force is exceeded. The first predetermined threshold of force can be greater than the second predetermined threshold of force, or vice versa.

In the illustrated embodiment, the frangible members 322 are thin wires comprising a weaker material than the material forming the body 310. In other embodiments, the frangible members can be, for example, cables, shafts, and/or sutures. The thin wires can be configured to break when a force greater than a predetermined threshold of force is applied. In other embodiments, the frangible members 322 can comprise, for example, a crack and/or a perforated region configured to make the frangible member 322 relatively weaker than the body 310. In still other embodiments, such as shown in FIG. 12, the frangible members 322 can comprise a strut portion 324 and a thinner portion 326 configured to break under a force exceeding a predetermined threshold. The strut portion 324 can have a first width $W_1$ and the thinner portion 326 can have a second width $W_2$ thinner than the first width.

In still other embodiments, when a force greater than a predetermined threshold of force is applied, the frangible members 322 can be configured to deform in a circumferential direction (e.g., by stretching) and remain permanently in the deformed configuration. For example, the frangible members 322 can be configured as springs and/or other biasing members such as deformable polymeric members.

In some embodiments, the frangible members 322 can comprise radiopaque portions. For example, the radiopaque portions can be disposed such that when the frangible member 322 breaks, the radiopaque portion splits into two radiopaque portions allowing a physician to determine that the frangible member 322 has been broken. For example, as the prosthetic valve is radially expanded, the physician can visualize the belt 304 using fluoroscopy. When the force applied to the belt 304 exceeds a first predetermined threshold of force, a first frangible member 322 comprising a radiopaque portion can break, splitting the radiopaque portion into two pieces. The physician can see the break in the visualization and can thus determine the amount of radial force that is being applied by the prosthetic valve to the native annulus and the diameter of the prosthetic valve. In other embodiments, the radiopaque portions can comprise a pattern configured to allow a physician to determine when the frangible member 322 has been broken.

In some embodiments, each extension member 318 can comprise a radiopaque portion. In other embodiments, only the frangible members 322 can comprise radiopaque portion. The radiopaque portions can comprise, for example, gold, platinum, radiopaque Nitinol, and/or combinations thereof.

In some embodiments, the belt 304 can comprise a cover configured to prevent the frangible members 322 from scratching and/or damaging the native annulus upon breaking. In some embodiments, the outer skirt of the prosthetic valve (e.g., outer skirt 70) can be configured as a cover. For example, the belt 304 can be disposed between the frame 302 and the outer skirt.

In some or all of the disclosed embodiments, in addition to belt 304, the prosthetic valve 300 can comprise one or more additional belts positioned at different locations along the longitudinal axis A of the prosthetic valve 300. The belts 304 can have, for example, differing predetermined diameters and/or differing predetermined thresholds for frangible member 322 breakage. In some embodiments, the prosthetic valve 300 can include a first belt 304 at an inflow end portion 306 of the frame and a second belt 304 at an outflow end portion 308 of the frame. In other embodiments, the prosthetic valve 300 can include two belts 304 positioned adjacent the inflow end portion 306 and/or the outflow end portion 308.

In a specific method for implanting a prosthetic heart valve 300 comprising one or more belts 304 in a patient's heart, a physician can use conventional techniques and/or devices to measure the approximate size of the native heart valve to facilitate selection of a desired size for the prosthetic heart valve 300. The prosthetic heart valve 300 can be mounted to the distal end portion of a delivery apparatus. The distal end portion of the delivery apparatus (along with the prosthetic valve 300) can be advanced through the patient's vasculature toward the native aortic valve. Once the prosthetic heart valve 300 is positioned at the desired implantation location (typically within the native aortic annulus), the prosthetic heart valve can be deployed (e.g., radially expanded).

To deploy the prosthetic valve, the physician can actuate the delivery apparatus, which can actuate one or more actuators (e.g., actuators 50 described above) coupled to the prosthetic valve 300. Each actuator can, for example, decrease the distance between the attachment locations of a respective sleeve and nut, causing the frame 302 to fore-shorten axially and expand radially. The prosthetic valve 300 (including belt 304) can continue to expand radially until it reaches a first predetermined diameter, at which belt 304 can no longer expand. The physician can then evaluate the fit of the prosthetic valve within the native annulus and determine the force applied by the prosthetic valve 300 to the native annulus using the first predetermined diameter.

In some embodiments, the belt 304 can provide tactile feedback to the physician during the implantation process. For example, the physician may be able to feel (e.g., via the handle of the delivery device) when a frangible member 322 breaks.

If further expansion of the prosthetic valve is required, the prosthetic valve 300 can be expanded by continuing to actuate the actuators such that the prosthetic valve expands and applies a force to the belt 304 until a predetermined threshold of force is exceeded, causing a first frangible member 322 to break and allowing the belt 304 and therefore the prosthetic valve 300 to expand to a second predetermined diameter. The physician can then re-evaluate the fit of the prosthetic valve within the native annulus and recalculate the force applied to the native annulus. This process can be repeated as necessary until the prosthetic valve 300 is expanded to a diameter that best fits the native annulus. For example, the prosthetic valve 300 desirably is expanded to a diameter sufficient to anchor the prosthetic valve in place against the surrounding tissue with minimal or no paravalvular leakage and without over-expanding and rupturing the native annulus.

Referring now to FIG. 13, in an alternative embodiment, the prosthetic valve 300 can comprise a belt 400. The belt 400 can be used in lieu of or in addition to belt 304, and can be disposed around a circumference of the prosthetic valve 300.

The belt 400 can comprise an elongated member 402 having a first end portion 404 and a second end portion 406 comprising a retaining member 408. The belt 400 can comprise a plurality of stoppers 410, spaced apart from each other along at least a portion of the elongated member 402. The elongated member 402 can be, for example, a cable, a wire, and/or a suture. In the illustrated embodiment, the stoppers 410 are configured as a plurality of spheres disposed on the elongated member 402. In other embodiments, the stoppers 410 can have any of various shapes.

The elongated member 402 can be looped such that the first end portion 404 extends through the retaining member 408, forming an annular shape around the circumference of the prosthetic valve 300. In some embodiments, the elongated member 402 can include a stopper-less portion along which the retaining member 408 can slide during expansion of the prosthetic valve. The position of the stoppers 410 and the length of the stopper-less portion can be selected to provide a first diameter for the frame 302 of the prosthetic valve.

In some embodiments, such as the illustrated embodiment, the stoppers 410 can be secured to the elongated member 402 at spaced apart locations using a second elongated member configured as a securing member 412. In other embodiments, the stoppers 410 can be formed integrally with the elongated member 402.

As shown in FIG. 13, the retaining member 408 can comprise a ring or loop formed along the end portion 406. The loop can be sized such that it has an opening equal to or slightly smaller than the diameter of a stopper 410. Accordingly, a sufficient force must be applied to force the stopper 410 to pass through the retaining member 408, as described in more detail below. In other embodiments, the retaining member 408 can have any of various shapes corresponding to the shape of the stoppers 410 and configured to allow a stopper 410 to pass through the retaining member 408 when a sufficient force is applied.

As the prosthetic valve 300 is expanded (increasing the circumference of the elongated member 402), the retaining member 408 can slide along the stopper-less portion 416 of the elongated member 402 until it reaches the first stopper (e.g., stopper 410a in the illustrated embodiment). The first stopper 410a prevents the retaining member 408 from continuing to slide along the elongated member 402, thereby retaining the belt 400 (and therefore the prosthetic valve 300) at a first predetermined diameter. A first radial force exerted by the prosthetic valve 300 on the native annulus can be determined based at least in part on the known mathematical relationship between the prosthetic valve's diameter and the radial force exerted by the prosthetic valve.

As the prosthetic valve 300 continues to expand (e.g., using actuators 50) the frame 302 applies an increasingly greater force to the belt 400. When the force exceeds a first predetermined threshold the first stopper 410a can pass through the retaining member 408, allowing the retaining member to slide along the first elongated member 402 until it reaches the second stopper 410b, which holds the belt 400 at a second predetermined diameter. A second force exerted by the prosthetic valve 300 on the native annulus can be determined as described previously.

As the actuators (e.g., actuators 50 described previously) continue to expand the prosthetic valve 300, the prosthetic valve 300 will continue to apply an increasingly greater force to the belt 400. When the force exceeds a second predetermined threshold (which can be greater than or equal to the first predetermined threshold) the second stopper 410b can pass through the retaining member 408, allowing the retaining member 408 to slide along the elongated member until it reaches the third stopper 410c, which holds the belt 400 at a third predetermined diameter. Each time a stopper 410 passes through the retaining member 408, the diameter of the belt 400 (and therefore the diameter to which the frame 302 can expand) increases. The process of expansion can continue until the prosthetic valve has reached a selected size. Throughout the implantation procedure, a physician can continuously monitor the diameter of the valve to determine when the prosthetic valve is at the diameter that best fits the native annulus and when the optimal amount of radial force is being applied by the prosthetic valve to the native annulus. In some embodiments, the belt 400 can provide tactile feedback to the physician during the implantation process. For example, the physician may be able to feel (e.g., via the handle of the delivery device) when the retaining member 408 contacts a stopper 410 and/or when the retaining member 408 moves past a stopper 410.

In some embodiments, the stopper 410 positioned at the end of first end portion 404 can be configured as an enlarged stopper 414. The enlarged stopper 414 can have a diameter greater the other stoppers 410 and greater than the opening of the retaining member 408 such that the enlarged stopper 414 is prevented from passing through the retaining member 408. The enlarged stopper 414 can have a diameter large enough that no amount of force applied by the prosthetic valve 300 is sufficient to cause the enlarged stopper to pass through the retaining member 408. In this way, the enlarged stopper 414 can create a maximum diameter beyond which the prosthetic valve 300 is prevented from expanding.

In some embodiments, one or more of the stoppers 410 and/or the retaining member 408 can comprise radiopaque portions. As the prosthetic valve is radially expanded, the physician can visualize the belt 400 using fluoroscopy and can determine the diameter of the prosthetic valve 300 based on the position of the stoppers 410 relative to the retaining member 408. For example, in a particular instance, the physician can determine that two stoppers 410 have passed through the retaining member 408 and thereby determine that the prosthetic valve is expanded to a third predetermined diameter. The physician can then determine the radial force exerted by the prosthetic valve based at least in part on the known mathematical relationship between the prosthetic valve's diameter and the radial force exerted by the prosthetic valve.

In another alternative embodiment, the belt can comprise a ratcheting mechanism. For example, an exemplary embodiment of a belt can comprise an elongated member extending around a circumference of the prosthetic valve and having a first end portion and a second end portion. The second end portion can comprise a ratcheting mechanism. In some embodiments, the first end portion can comprise a plurality of teeth or other feature configured to interact with the ratcheting mechanism.

The elongated member can be looped such that the first end portion extends through the ratcheting mechanism, forming an annular shape around the circumference of the prosthetic valve. As the prosthetic valve expands, the first end portion can move relative to the ratcheting portion until a first predetermined diameter is reached, at which point the ratcheting mechanism can engage the first end portion and prevent further expansion of the prosthetic valve. The ratcheting mechanism can be configured to retain the valve at the first predetermined diameter until a force greater than a first predetermined threshold is applied to the belt. When the force applied by the prosthetic valve exceeds the first predetermined threshold the ratcheting member can allow the first end portion to move relative to the ratcheting member until a second predetermined diameter is reached. The process of expansion can continue until the prosthetic valve has reached a selected size.

Referring now to FIG. 14, in an alternative embodiment, the prosthetic valve 300 can comprise a belt 500. The belt 500 can be used in lieu of or in addition to belts 304 and 400, and can be disposed around a circumference of the prosthetic valve 300. Belt 500 can be similar to belt 304 except that the body 501 of belt 500 comprises a plurality of rings 502 rather than a plurality of alternating peaks and valleys.

The belt 500 can comprise an annular body portion 501 comprising a plurality of hoops or rings 502. As shown in the illustrated embodiment, each ring 502 can have a substantially oval shape including a first end portion 504, a second end portion 506, and first and second central portions 508, 510 each extending between the first and second end portions. In other embodiments, the rings 502 can have any of various shapes, including but not limited to circles, squares, rectangles, triangles, diamonds, square-ovals, etc. The belt 500 can be made of any of the materials discussed above with regard to belt 304.

Each ring 502 can be coupled to one or more adjacent rings at the first and/or second central portions 508, 510. In other embodiments, each ring 502 can be coupled to one or more adjacent rings at the first and/or second end portions 504, 506.

The belt 500 can be radially compressible and expandable between a radially compressed state and a radially expanded state (FIG. 14). When the belt 500 is in the radially expanded position, the circumferential length between the first and second central portions 508, 510 of a respective ring 502 can be greater than the circumferential length between the first and second central portions 508, 510 of the respective ring when in the radially compressed position.

The belt 500 can comprise a plurality of circumferentially-extending extension members 512 extending between adjacent portions of the body 501. For example, in the illustrated embodiment, the extension members 512 extend between the first and second central portions 508, 510 of each ring 502. However, in other embodiments, the extension members 512 can extend between the first end portions 504 of adjacent rings, between the second end portions 506 of adjacent rings, and/or any combination of the foregoing.

One or more selected extension members 512 can be configured as frangible members 514, similar to frangible members 322 described above. The one or more frangible members 514 can be configured to break, rupture, or otherwise deform, such as by stretching, when a force (e.g., a radial force) greater than a predetermined threshold of force is applied to the belt 500, for example, by the prosthetic valve 300.

As the prosthetic valve 300 expands, the belt 500 expands radially with the frame from a compressed diameter until it reaches a first predetermined diameter. As the prosthetic valve 300 continues to expand, the frame 302 applies an increasingly greater radial force to the belt 500. When the force exceeds a first predetermined threshold, a first frangible member 514 can break, allowing the belt 500 to radially expand to a second predetermined diameter. A first radial force exerted by the prosthetic valve 300 on the native annulus can be determined based at least in part on the known mathematical relationship between the prosthetic valve's diameter and the radial force exerted by the prosthetic valve.

As the prosthetic valve 300 continues to expand, the frame 302 applies an increasingly greater force to the belt 500, which is now expanded to the second predetermined diameter. When the force exceeds a second predetermined threshold (which can be greater than or equal to the first predetermined threshold) a second frangible member 514 can break, allowing the body 501 to radially expand to a third predetermined diameter. Each time a frangible member 514 breaks, the diameter of the belt 500 (and therefore the diameter to which the frame 302 can expand) increases. The process of expansion and breakage can continue until the prosthetic valve has reached a selected size.

FIG. 15 illustrates a delivery apparatus 600, according to one embodiment, adapted to deliver a prosthetic heart valve 602, such as any of the prosthetic heart valves described herein. The prosthetic valve 602 can be releasably coupled to the delivery apparatus 600. It should be understood that the delivery apparatus 600 and other delivery apparatuses disclosed herein can be used to implant prosthetic devices other than prosthetic valves, such as stents or grafts.

The delivery apparatus 600 in the illustrated embodiment generally includes a handle 604, and a first elongated shaft 606 (which comprises an outer shaft in the illustrated embodiment) extending distally from the handle 604.

In embodiments wherein the prosthetic valve 602 is a mechanically-expandable prosthetic valve, such as the embodiment illustrated in FIG. 15, the delivery apparatus 600 can comprise at least one actuator assembly 608 extending distally through the outer shaft 606. The at least one actuator assembly 608 can be configured to radially expand and/or radially collapse the prosthetic valve 602 when actuated. Though the illustrated embodiment shows two actuator assemblies 608 for purposes of illustration, it should be understood that one actuator 608 can be provided for each actuator on a corresponding prosthetic valve. For example, three actuator assemblies 608 can be provided for a prosthetic valve having three actuators. In other embodiments, a greater or fewer number of actuator assemblies can be present.

The actuator assemblies 608 can be releasably coupled to the prosthetic valve 602. For example, in the illustrated embodiment, each actuator assembly 608 can be coupled to a respective actuator of the prosthetic valve 602. Each actuator assembly 608 can comprise, for example, a support tube, an actuator member, and a locking tool. When actuated, the actuator assembly can transmit pushing and/or pulling forces to portions of the prosthetic valve to radially expand and collapse the prosthetic valve. The actuator assemblies 608 can be at least partially disposed radially within, and extend axially through, one or more lumens of the outer shaft 606. For example, the actuator assemblies 608 can extend through a central lumen of the shaft 606 or through separate respective lumens formed in the shaft 606.

In embodiments wherein the prosthetic valve 602 is a self-expanding prosthetic valve or a balloon-expandable prosthetic valve, the delivery apparatus 600 need not include actuators 608.

In some embodiments, a distal end portion 616 of the shaft 606 can be sized to house the prosthetic valve in its radially compressed, delivery state during delivery of the prosthetic valve through the patient's vasculature. In this manner, the distal end portion 616 functions as a delivery sheath or capsule for the prosthetic valve during delivery.

The handle 602 of the delivery apparatus 600 can include one or more control mechanisms (e.g., knobs or other actuating mechanisms) for controlling different components of the delivery apparatus 600 in order to expand and/or deploy the prosthetic valve 602. For example, in the illustrated embodiment the handle 602 comprises first, second, and third knobs 610, 612, and 614.

The first knob 610 can be a rotatable knob configured to produce axial movement of the outer shaft 606 relative to the prosthetic valve 602 in the distal and/or proximal directions in order to deploy the prosthetic valve from the delivery sheath 616 once the prosthetic valve has been advanced to a location at or adjacent the desired implantation location with the patient's body. For example, rotation of the first knob 610 in a first direction (e.g., clockwise) can retract the sheath 616 proximally relative to the prosthetic valve 602 and rotation of the first knob 610 in a second direction (e.g., counter-clockwise) can advance the sheath 616 distally. In other embodiments, the first knob 610 can be actuated by sliding or moving the knob 610 axially, such as pulling and/or pushing the knob. In other embodiments, actuation of the first knob 610 (rotation or sliding movement of the knob 610) can produce axial movement of the actuator assemblies 608 (and therefore the prosthetic valve 602) relative to the delivery sheath 616 to advance the prosthetic valve distally from the sheath 616.

In some embodiments, the second knob 612 can be a rotatable knob configured to produce radial expansion and/or contraction of the prosthetic valve 602. Rotation of the second knob 612 in a first direction (e.g., clockwise) can radially expand the prosthetic valve 602 and rotation of the second knob 612 in a second direction (e.g., counter-clockwise) can radially collapse the prosthetic valve 602. In other embodiments, the second knob 612 can be actuated by sliding or moving the knob 612 axially, such as pulling and/or pushing the knob.

In some embodiments, the third knob 614 can be a rotatable knob configured to retain the prosthetic heart valve 602 in its expanded configuration. Rotation of the third knob in a first direction (e.g., clockwise) can, for example, rotate each locking tool to advance the locking nuts to their distal positions to resist radial compression of the frame of the prosthetic valve. Rotation of the knob 614 in the opposite direction (e.g., counterclockwise) can rotate each locking tool in the opposite direction to decouple each locking tool from the respective nut and remove the locking tool from the respective actuator screw. In other embodiments, the third knob 614 can be actuated by sliding or moving the third knob 614 axially, such as pulling and/or pushing the knob.

Although not shown, the handle 604 can include a fourth rotatable knob operative connected to a proximal end portion of each actuator member. The fourth knob can be configured to rotate each actuator member, upon rotation of the knob, to unscrew each actuator member from the proximal portion of a respective actuator. Once the locking tools and the actuator members are unscrewed from the actuator screws, they can be removed from the patient along with the support tubes.

In some embodiments, in lieu of or in addition to a valve belt such as valve belts 304, 400, or 500, a prosthetic valve 700 having a frame 702 can comprise one or more restriction members/belts/bands 704 configured to prevent the expansion of the prosthetic valve 700 past a selected diameter. Though the illustrated prosthetic valve 700 is a self-expanding prosthetic valve, it should be understood that such restriction bands 704 can be used with any type of prosthetic valve, including mechanical valves such as disclosed in U.S. Provisional Application No. 63/085,947, filed Sep. 30, 2020 and U.S. Pat. No. 10,603,165, balloon-expandable prosthetic heart valves, such as disclosed in U.S. Publication Nos. U.S. 2018/0028310 and U.S. 2012/0123529, and self-expandable prosthetic heart valves, such as disclosed in U.S. Publication No. 2015/0157455.

Prosthetic valve 700 comprises a frame 702 having an inflow end portion 706 and an outflow end portion 708, and can include a valvular structure 703 (FIG. 17) (similar to valvular structure 18) and an inner skirt 718 (FIG. 17). In some embodiments, the prosthetic valve 700 can further comprise one or more outer skirts, as previously described, through these components are omitted for purposes of illustration. The frame 702 can comprise a plurality of struts 710 coupled together in an open lattice pattern defining a plurality of cells 712.

As shown in FIG. 16, the restriction band 704 can extend around a circumference of the frame 702. The restriction band 704 can be configured to expend to a maximum diameter $D_M$, such that the band allows expansion of the frame 702 to the maximum diameter $D_M$ and prevents further expansion of the frame 702 past the maximum diameter $D_M$. In some embodiments, the restriction band 704 can comprise, for example, a resilient cloth. The restriction band 704 can have a length $L_1$ extending axially along a longitudinal axis A of the frame 702. In other embodiments, the band 704 can have a greater or shorter width. For example, in some embodiments, the restriction band 704 can extend along substantially the entire length of the prosthetic valve 700, thereby uniformly restricting the maximum expansion of the prosthetic valve along its length.

In some embodiments, the restriction band 704 can comprise fibers woven such that they extend at a non-parallel and non-perpendicular angle relative to the inflow edge 714 and/or outflow edge 716 of the band 704. For example, the fibers can be woven such that they are oriented at a 45 degree angle relative to the outflow and inflow edges 714, 716. Such a configuration allows the restriction band 704 to elongate the in the axial and/or circumferential direction with the movement of the frame 702.

As mentioned, the prosthetic valve 700 can be a self-expanding prosthetic valve. In some embodiments, the prosthetic valve 700 can be deployed to a diameter less than the maximum diameter $D_M$ of the restriction band 704 during implantation (e.g., such that the band 704 does not restrict expansion and/or is not fully tensioned around the prosthetic valve 700). For example, the maximum diameter $D_M$ can be greater than the diameter of the native annulus. In such embodiments, if the native annulus loses tension over time, thereby allowing prosthetic valve 700 to further self-expand, the restriction band 704 can function to prevent expansion of the prosthetic valve 700 beyond the maximum diameter $D_M$ of the restriction band. Such a configuration advantageously mitigates the risk of delayed coronary obstruction (DCO) by preventing expansion past the maximum selected diameter $D_M$ even if the force applied by the native annulus lessens. The force applied by the restriction band 704 at the maximum diameter $D_M$ can be greater than the radial expansion force of the self-expandable valve.

In some embodiments, a physician may be provided with a variety of prosthetic valves each comprising a restriction band 704 having a different selected maximum diameter $D_M$. Accordingly, the physician can choose the appropriate prosthetic valve/restriction band combination having a maximum diameter $D_M$ best suited to the patient's specific anatomy. In other embodiments, a physician can select a specific restriction band 704 to be attached to a pre-assembled prosthetic valve.

Though in the illustrated embodiment, the restriction band 704 is positioned at a central position along a longitudinal axis A of the frame 702, in other embodiments, the restriction band 304 can be positioned nearer to or further from the outflow and/or inflow ends 706, 708. For example, in some embodiments, the prosthetic valve 700 can comprise a restriction band 704 positioned at the outflow end portion 708 of the frame 702 (e.g., defining an A-shape). Such a configuration can advantageously restrict the outflow end portion 708 from expanding and potentially obstructing the native coronaries, while still allowing the inflow end portion 706 of the prosthetic valve to expand freely to a larger diameter within the native annulus, preventing or mitigating prosthetic valve migration if the tension of the native annulus decreases over time. In another example, the prosthetic valve 700 can comprise a restriction band 704 positioned at the inflow end 706 of the frame 702 (e.g., defining a V-shape). Such a configuration can advantageously limit over-expansion of the inflow end portion 706, thereby preventing or mitigating the risk of anatomical rupture. In still other examples, the prosthetic valve 700 can comprise a restriction band at the outflow end portion 708 and the inflow end portion 706, defining a barrel-shaped frame. Such a configuration can advantageously prevent the outflow end portion 708 from obstructing the coronary ostia while also preventing over expansion of the prosthetic valve 700 against the native annulus to mitigate risks of tissue damage or conduction disturbances.

Though the illustrated embodiment shows only one restriction band 704, in other embodiments, a prosthetic valve 700 can comprise a plurality of restriction bands 704. The plurality of restriction bands 704 can be disposed along the longitudinal axis A of the prosthetic valve 700 in any of various configurations. In some embodiments, the restriction bands 704 can be spaced apart from one another along the longitudinal axis A of the frame 702. In other embodiments, the restriction bands 704 can be disposed such that they fully or partially overlap one or more adjacent bands 704.

In some embodiments, the restriction band 704 can be coupled to the prosthetic valve 700 during assembly of the prosthetic valve. For example, in some embodiments, as shown in FIG. 17, the restriction band 704 can be coupled to the prosthetic valve 700 by suturing the restriction band 704 to an inner skirt 718 using one or more sutures 720. However, in other embodiments, the restriction band 704 can be, for example, sutured directly to the frame 702 (e.g., along struts 710 of the frame, and/or at junctions 722 of the frame) using suture loops that extend around the struts 710 and/or junctions 722 of the frame.

Referring to FIG. 18, in some embodiments, the restriction band 704 can be configured as a belt 724 comprising a wire, string, and/or cable. The belt 724 can extend circumferentially around the frame 702. In some embodiments, as shown in FIG. 18, the belt 724 can be coupled to the frame 702 by, for example, weaving the belt 724 through the cells 712 of the frame in an in-and-out pattern. In other embodiments, the belt 724 can be coupled to the frame 702 via a plurality of sutures. In still other embodiments, the frame 702 can comprise a plurality of eyelets or apertures through which portions of the belt 724 can be threaded.

In some embodiments, the belt 724 can comprise multiple strands of material. For example, in the illustrated embodiment, the belt 724 comprises a first strand 726 and a second strand 728. The first strand 726 can be woven through the cells 712 of the frame 702 in an in-and-out pattern such that portions of the first strand 726 are disposed on a radially outer surface 730 of the frame 702 and other portions of the first strand 726 are disposed on the radially inner surface 732 of the frame 702. The second strand 728 can likewise be woven through the cells 712 of the frame in an in-and-out pattern. In some embodiments, the second strand 728 can be woven such that, at least in parts, it opposes the first strand 726. For example, at selected circumferential points on the frame 702 the first strand 726 can be disposed on the radially outer surface 730 and the second strand 728 can be disposed on the radially inner surface 732.

Referring now to FIG. 19, in some embodiments, the prosthetic valve 700 can comprise a plurality of restriction belts or bands 734, each comprising a different maximum diameter $D_M$ configured such that a physician can select the appropriate maximum diameter $D_M$ for a patient.

As shown in FIG. 19, in some embodiments, the prosthetic valve 700 can comprise three restriction bands 734*a*, 734*b*, 734*c*. The first restriction band 734*a* can have a first maximum diameter $D_{M1}$, the second restriction band 734*b* can have a second maximum diameter $D_{M2}$ greater than the first maximum diameter $D_{M1}$, and the third restriction band 734*c* can have a third maximum diameter $D_{M3}$ greater than both the first and second maximum diameters $D_{M1}$ and $D_{M2}$. In other embodiments, a prosthetic valve 700 can comprise a greater or fewer number of restriction bands 734.

In some embodiments, one or more of the restriction bands 734 can be configured as a belt comprising a wire, string, and/or cable, and/or can comprise a resilient cloth similar to restriction band 704. In some embodiments, each restriction band 734 can comprise the same material. However, in other embodiments, one or more restriction bands 734 can comprise different materials.

In use, a physician may analyze the patient's specific anatomy (e.g., using angiograms and/or CT-scans) prior to the implantation procedure, and can select an appropriate maximum diameter $D_M$ for the inflow end portion and/or the outflow end portion of the frame. The physician can then cut, sever, or otherwise remove any restriction band 734 having a maximum diameter $D_M$ less than that of the selected maximum diameter. Accordingly, once the prosthetic valve has been delivered to the implantation site using a delivery apparatus such as delivery apparatus 600 and the distal end portion 616 has been retracted, the inflow and/or outflow end portion of the prosthetic valve 700 can self-expand to a diameter not greater than the selected maximum diameter.

In some embodiments, the prosthetic valve 700 can comprise a plurality of restriction bands 734 positioned at the outflow end portion 708 and a plurality of restriction bands 734 positioned at the inflow end portion 706. By cutting any restriction bands 734 having a maximum diameter less than the selected maximum diameter, the physician can select a maximum diameter (e.g., based on the patient's specific anatomy as determined by the angiograms and/or CT-scans) for each the inflow end portion 706 and the outflow end portion 708 of the prosthetic valve. Such a configuration can advantageously prevent the outflow end portion 708 of the prosthetic valve 700 from obstructing the coronary ostia while also preventing over expansion of the prosthetic valve 700 against the native annulus to mitigate risks of tissue damage or conduction disturbances. In some embodiments, the physician can select restriction bands having the same maximum diameter for each the inflow and outflow end portions (e.g., to define a cylindrical or barrel-shape for the frame), however, in other embodiments, the physician can select restriction bands having different maximum diameters for each the inflow and outflow end portions (e.g., to define an A-shape or a V-shape for the frame).

In other embodiments, the restriction band 734 can be a single band that has discrete release levels (e.g., similar to belts 304, 400, and 500 described previously). One or more of such restriction bands 734 can be disposed around the frame 702. For example, a first band can be positioned at an inflow end portion and a second band can be positioned at an outflow end portion. In such embodiments, the physician may analyze the patient's specific anatomy as described previously to determine a selected inflow end diameter and a selected outflow end diameter for the prosthetic valve. So determined, the physician can partially release the first and second restriction bands (e.g., by severing or breaking portions of the bands, and/or by using a ratcheting mechanism) such that each band can expand to the selected maximum diameter. In some embodiments, the physician can release the restriction bands such that the same maximum diameter is selected for each the inflow and outflow end portions (e.g., to define a cylindrical or barrel-shape for the frame), however, in other embodiments, the physician can release the restriction bands such that they have different maximum diameters for each the inflow and outflow end portions (e.g., to define an A-shape or a V-shape for the frame).

The restriction band embodiments described herein advantageously improve usability of the prosthetic valves by providing a wide range of potential maximum diameters to which a prosthetic valve can be expanded without requiring the physician to stock and maintain a wide variety of prosthetic valves. When mechanically-expandable valves are used, a physician cannot always determine the diameter of the prosthetic valve in real time during the expansion process. Use of one or more restriction bands, such as bands 704, 724, and/or 734, can prevent inadvertent over-expansion of the mechanically expandable prosthetic valve past the selected maximum diameter. Likewise, when balloon-expandable valves are used, use of one or more restriction bands can prevent inadvertent over-expansion of the balloon-expandable prosthetic valve past the selected maximum diameter.

In some embodiments, such as shown in FIG. 19, each restriction band 734 of the plurality of restriction bands can be coupled to the same portion of the prosthetic valve 700 (for example, the central portion, the outflow end portion, and/or the inflow end portion) and can be spaced axially in close proximity to the other restriction bands. The space between each band and the one or more adjacent bands 734 can be selected to allow easy cutting/removal of the un-selected band(s) (e.g., using scissors).

In the illustrated embodiment, the restriction bands 734 are coupled to the prosthetic valve 700 by weaving the restriction bands 734 through the cells 712 of the frame 702 in an in-and-out pattern. To remove any undesired restriction bands 734, the physician can cut through the band itself. In other embodiments, each of the plurality of restriction bands 734 can be coupled to prosthetic valve 700 at a plurality of discrete attachment points using, for example, suture loops. For example, a restriction band 734 can be coupled to the prosthetic valve 700 using two circumferentially opposing suture loops. In such embodiments, a physician can cut the two suture loops in order to remove the restriction band 734.

Referring now to FIGS. 20-21, in lieu or in addition to a valve belt such as valve belts 304, 400, or 500, a prosthetic valve 800 having a frame 802 can comprise a flexible tension member 804 configured to allow controllable gradual valve expansion. The tension member 804 can apply a radially inwardly directed force to the frame 802 that can be gradually lessened such that the frame can expand at a controlled rate (e.g., a rate selected by the physician) to a selected diameter.

Though the illustrated prosthetic valve 800 is a mechanically-expandable prosthetic valve, it should be understood that the tension members 804 described herein can be used with any type of prosthetic valve, including mechanical valves such as those disclosed in U.S. Provisional Application No. 63/085,947, filed Sep. 30, 2020 and U.S. Pat. No. 10,603,165, balloon-expandable prosthetic heart valves, such as those disclosed in U.S. Publication Nos. U.S. 2018/0028310 and U.S. 2012/0123529, and self-expandable prosthetic heart valves, such as those disclosed in U.S. Publication No. 2015/0157455.

Prosthetic valve 800 comprises a frame 802 having an inflow end portion 806 and an outflow end portion 808, and can include a valvular structure (e.g., valvular structure 18) and inner and/or outer skirts, as previously described, through these components are omitted for purposes of illustration. The frame 802 can comprise a plurality of struts 810 coupled together at junctions 812 in a lattice pattern defining a plurality of cells 814. The prosthetic valve 800 can have a self-expanding range, e.g., the frame 802 can inherently self-expand from a fully crimped diameter to a partially expanded diameter, and a mechanically expandable range, e.g., the frame 802 can be mechanically expanded from the partially expanded diameter to a fully expanded diameter. The prosthetic valve 800 can comprise one or more expansion and locking mechanisms 816 (e.g., three) configured to mechanically expand the frame 802 from the partially expanded diameter to the fully expanded diameter and to lock the frame 802 in the radially expanded configuration.

As shown in FIG. 20, the flexible tension member 804 can have a first end portion 818 releasably coupled to the frame 802 at a first location and a second end portion 820 coupled to the handle of the delivery apparatus (e.g., handle 604 of apparatus 600 shown in FIG. 15). The handle 604 can include a knob or other actuation mechanism operatively coupled to the tension member 804 to apply a force (e.g., a proximally directed force) to the tension member 804. In the illustrated embodiment, the first end portion 818 is coupled to the frame at a location adjacent the inflow end portion 806. However, in other embodiments, the first end portion 818 can be coupled to the frame 802 at any axial location along the length of the frame and at any location circumferentially around the frame 802.

The tension member 804 can extend at least partially around the circumference of the frame 802. For example, the tension member 804 can be disposed such that it extends around the frame 802 in a continuous helical manner defining a plurality of loops 820. In in illustrated embodiment, the tension member 804 extends helically around the frame 802 such that it defines three loops 820. However, in other embodiments, the tension member 804 can define a greater or fewer number of loops, for example, a single loop. In still other embodiments, the tension member 804 can be disposed such that it spans a distance less than the full circumference of the frame 802.

As shown in FIG. 20, in some embodiments, the tension member 804 can be coupled to the frame 802 by weaving the tension member through selected cells 814 of the frame 802 in an in-and-out manner. At points, the tension member 804 can extend over the radially outer surface 822 of the frame, and at other points the tension member 804 can extend over the radially inner surface 824 of the frame. In some embodiments, portions of the tension member 804 can pass between the radially inner surface 824 of the frame and a radially outer surface 826 of one or more expansion and locking mechanisms 816. In other embodiments, the tension member 804 can be coupled to the frame 802 at selected attachment points by, for example, passing the tension member 804 through one or more eyelets and/or openings formed in the struts 810 and/or at the junctions 812 between the struts 810, etc.

The tension member 804 can be, for example, a suture (e.g., a single filament suture or a multi-filament suture), a flexible wire (e.g., a metal wire formed from stainless steel, Nitinol or other suitable metals), a cable (e.g., a braided cable formed from metal or polymeric strands) or any other similar materials that can be threaded through the frame 802 and placed in tension to radially compress the prosthetic valve as described herein.

In the illustrated embodiment, the first end portion 818 of the tension member 804 is releasably coupled to the frame 802 using one or more knots 828. However, in other embodiments, the tension member 804 can be releasably coupled to the frame using one or more clips, hooks, and/or other such releasable mechanisms. In some embodiments, an optional sheath or tube can extend over the second end portion 820 of the tension member 804.

In some embodiments, the tension member 804 can pass through a locking component coupled to the frame 802. The locking component can be configured to retain the tension member 804 at a selected tension thereby retaining the frame 802 at a selected diameter. Such a configuration can advantageously prevent or mitigate further spontaneous radial expansion of the prosthetic valve.

The tension member 804 can be used to gradually allow expansion of the prosthetic valve 800 in the following exemplary manner. The prosthetic valve 800 can be connected a delivery apparatus, such as delivery apparatus 600 described previously. The distal end portion of the delivery apparatus 600 (along with prosthetic valve 800) can be advanced through the vasculature of a patient to a selected implantation site.

Once at the implantation site, the distal end portion 616 of the shaft 606 covering the prosthetic valve 800 can be retracted, and the tension member 804 can be tensioned (e.g., using the handle 604) to prevent inherent expansion caused by the natural resiliency of the frame 802.

The tension member 804 can continue to be tensioned as one or more expansion forces are applied to the frame (e.g., using expansion and locking mechanisms 816). The tension in tension member 804 can be gradually released, allowing the frame to expand gradually (e.g., at a controlled rate) to a larger diameter and/or its fully expanded diameter. Such a configuration can advantageously prevent or mitigate unintended radial expansion of the prosthetic valve (e.g., caused by inherent frame expansion) and/or control expansion to prevent radial "jumps" caused by, for example, stepped expansion mechanisms (e.g., expansion and locking mechanisms that utilize a ratchet system), thereby maximizing the physician's control over positioning the prosthetic valve.

In some embodiments, once the prosthetic valve 800 has been expanded, the tension in the tension member 804 can be fully released and the tension member 804 can be uncoupled from the frame 802. The delivery apparatus 600 can be released from the prosthetic valve 800 and removed from the body. In other embodiments, such as those comprising a locking component, the tension member 804 can be disconnected from the delivery apparatus 600 and can remain in the patient's body with the prosthetic valve 800.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A belt for an implantable prosthetic device, comprising:

an annular body including a plurality of alternating peaks and valleys;

a plurality of frangible members extending between at least one of adjacent peaks and adjacent valleys;

wherein the annular body is radially expandable from a radially compressed configuration to a first diameter upon application of a radially outwardly directed force via an expandable implantable prosthetic device; and wherein a first frangible member of the plurality of frangible members is configured to break when the radially outwardly directed force exceeds a first predetermined threshold to allow radial expansion of the annular body to a second diameter.

Example 2. The belt of any example herein, particularly example 1, wherein a second frangible member of the plurality of frangible members is configured to break when the radially outwardly directed force exceeds a second predetermined threshold to allow radial expansion of the annular body to a third diameter.

Example 3. The belt of any example herein, particularly of examples 1-2, wherein the plurality of frangible members comprise wires.

Example 4. The belt of any of any example herein, particularly examples 1-3, wherein the frangible members comprise at least one of a crack and a perforated region.

Example 5. An assembly, comprising:

an implantable prosthetic device comprising a frame movable between a radially compressed configuration and a radially expanded configuration; and a belt extending circumferentially around the frame, the belt configured to radially expand to a first diameter when a first force below a predetermined threshold is applied and expand to a second diameter when a second force greater than the predetermined threshold is applied.

Example 6. The assembly of any example herein, particularly example 5, wherein the belt comprises a plurality of frangible members and wherein a first frangible member is configured to break when the second force applied to the belt, allowing the belt to radially expand to the second diameter.

Example 7. The assembly of any of any example herein, particularly examples 5-6, the belt further comprising an annular body including a plurality of alternating peaks and valleys, the annular body being movable between a radially compressed configuration and a radially expanded configuration.

Example 8. The assembly of any example herein, particularly example 7, wherein each frangible member extends between at least one of adjacent peaks and adjacent valleys.

Example 9. The assembly of any example herein, particularly examples 6-8, wherein the predetermined threshold of force is a first predetermined threshold of force, and wherein a second frangible member is configured to break when a force greater than a second predetermined threshold of force is applied to the belt, allowing the belt to radially expand to a third diameter.

Example 10. The assembly of any example herein, particularly example 9, wherein the second predetermined threshold of force is equal to the first predetermined threshold of force.

Example 11. The assembly of any example herein, particularly examples 6-10, wherein the frangible members comprise wires.

Example 12. The assembly of any example herein, particularly examples 6-11, wherein the frangible members comprise at least one of a crack and a perforated region.

Example 13. The assembly of any example herein, particularly examples 6-10, wherein the frangible members comprise a strut portion and a thinner portion, the strut portion having a first width and the thinner portion having a second width smaller than the first width.

Example 14. The assembly of any example herein, particularly example 5, wherein the belt comprises an elongated member having a first end portion and a second end portion comprising a retaining member; and a plurality of stoppers disposed along at least a portion of the elongated member; wherein a first stopper is configured to pass through the retaining member when the second force is applied.

Example 15. The assembly of any example herein, particularly example 14, wherein the retaining member comprises a loop.

Example 16. The assembly of any example herein, particularly examples 14-15, wherein the predetermined threshold of force is a first predetermined threshold of force, and wherein a second stopper is configured to pass through the retaining member when a force greater than a second predetermined threshold of force is applied to the belt, allowing the belt to radially expand to a third diameter.

Example 17. The assembly of any example herein, particularly examples 14-16, wherein the stoppers have a substantially circular shape in cross-section.

Example 18. The assembly of any example herein, particularly examples 5-17, wherein the radial force applied by the prosthetic valve can be determined based at least in part on the diameter of the prosthetic valve.

Example 19. The assembly of any example herein, particularly examples 5-18, wherein the prosthetic device is a prosthetic heart valve comprising a plurality of leaflets that regulate the flow of blood through the frame.

Example 20. A method, comprising:

advancing an implantable prosthetic device comprising a belt to a selected implantation site inside the body of a patient, the belt extending around a circumference of the prosthetic device and comprising one or more frangible members;

radially expanding the prosthetic device and the belt to a first diameter;

applying a first expansion force greater than a predetermined threshold to the prosthetic valve to break a first frangible member; and radially expanding the prosthetic device and the belt to a second diameter.

Example 21. The method of any example herein, particularly example 20, further comprising determining a magnitude of a force applied by the prosthetic device to the selected implantation site based at least in part on the diameter of the prosthetic valve.

Example 22. The method of any example herein, particularly examples 20-21, further comprising applying a second expansion force greater than a second predetermined threshold to the prosthetic device to break a second frangible member; and radially expanding the prosthetic device and the belt to a third diameter.

Example 23. An implantable prosthetic device, comprising:

a frame movable between a radially compressed configuration and a radially expanded configuration, the frame having an inflow end portion and an outflow end portion; and a restriction band extending circumferentially around the frame, the restriction band configured to allow expansion of the frame to a selected diameter and to prevent expansion of the frame past the selected diameter.

Example 24. The implantable device of any example herein, particularly example 23, wherein the restriction band comprises a resilient cloth having a length extending axially along at least a portion of the longitudinal axis of the frame.

Example 25. The implantable device of any example herein, particularly examples 23-24, wherein the restriction band has a length extending along the entire length of the frame.

Example 26. The implantable device of any example herein, particularly examples 23-25, wherein the restriction band comprises fibers woven at a non-parallel and non-perpendicular angle relative to at least one of an inflow edge and an outflow edge of the restriction band.

Example 27. The implantable device of any example herein, particularly example 26, wherein the non-parallel and non-perpendicular angle is 45 degrees.

Example 28. The implantable device of any example herein, particularly examples 23-27, wherein the restriction band is disposed around the inflow end portion of the frame.

Example 29. The implantable device of any example herein, particularly examples 23-27, wherein the restriction band is disposed around the outflow end portion of the frame.

Example 30. The implantable device of any example herein, particularly examples 23-29, wherein the restriction band is a first restriction band and the implantable device further comprises a second restriction band disposed around at least one of the inflow end portion and the outflow end portion of the frame.

Example 31. The implantable device of any example herein, particularly examples 23-30, wherein the restriction band is coupled to the frame via one or more sutures.

Example 32. The implantable device of any example herein, particularly examples 23-30, wherein the implantable device further comprises an inner skirt disposed on a radially inner surface of the frame and wherein the restriction band is coupled to the inner skirt via one or more sutures.

Example 33. The implantable device of any example herein, particularly examples 23-32, wherein the restriction band comprises a belt comprising at least one of wire, string, and cable.

Example 34. The implantable device of any example herein, particularly example 33, wherein the belt is coupled to the frame by weaving the belt through one or more cells of the frame in an in-and-out pattern.

Example 35. A method, comprising:
selecting a maximum diameter for an implantable prosthetic device based at least in part on a patient's native anatomy, the prosthetic device comprising a frame and a plurality of restriction belts extending around a circumference of the frame, each belt having a different maximum diameter;
cutting any of the plurality of restriction belts having a maximum diameter less than the selected maximum diameter;
advancing the implantable prosthetic device to a selected implantation site inside the body of the patient; and
radially expanding the prosthetic device and the remaining restriction belts to the selected maximum diameter.

Example 36. The method of any example herein, particularly example 35, wherein the plurality of restriction belts comprises three belts.

Example 37. The method of any of example herein, particularly examples 35-36, wherein the implantable prosthetic device is self-expanding.

Example 38. The method of any example herein, particularly examples 35-36, wherein the implantable prosthetic device is mechanically expandable and comprises one or more expansion and locking mechanisms.

Example 39. The method of any example herein, particularly examples 35-36, wherein the implantable prosthetic device is balloon-expandable.

Example 40. The method of any example herein, particularly examples 35-39, wherein the plurality of belts is a first plurality of restriction belts disposed at the inflow end portion of the frame and wherein the prosthetic device further comprises a second plurality of belts disposed at the outflow end of the frame.

Example 41. The method of any example herein, particularly example 40, wherein determining the selected maximum diameter for the implantable prosthetic device based at least in part on a patient's native anatomy comprises determining a selected maximum diameter of the inflow end portion and a selected maximum diameter of the outflow end portion.

Example 42. The method of any example herein, particularly example 41, wherein the selected maximum diameter of the inflow end portion is greater than the selected maximum diameter of the outflow end portion.

Example 43. The method of any example herein, particularly example 41, wherein the selected maximum diameter of the inflow end portion is less than the selected maximum diameter of the outflow end portion.

Example 44. The method of any example herein, particularly examples 35-43, wherein the patient's native anatomy is determined using at least one of an angiogram and a CT-scan.

Example 45. An implantable prosthetic device, comprising:
a frame movable between a radially compressed configuration and a radially expanded configuration, the frame having an inflow end portion and an outflow end portion;
a tension member extending circumferentially around at least a portion of the frame, the tension member having a first end portion releasably coupled to the frame and a second end portion configured to be coupled to a handle of a delivery apparatus; and
wherein the tension member applies a radially inwardly directed force to the frame that can be gradually lessened such that the frame can expand at a controlled rate to a selected diameter.

Example 46. The implantable device of any example herein, particularly example 45, wherein the first end portion of the tension member is coupled to the inflow end portion of the frame.

Example 47. The implantable device of any example herein, particularly examples 45-46, wherein the tension member is coupled to the frame using a knot.

Example 48. The implantable device of any example herein, particularly examples 45-47, wherein the tension member extends helically around the circumference of the frame.

Example 49. The implantable device of any example herein, particularly example 48, wherein the tension member extends around the frame forming three loops.

Example 50. The implantable device of any example herein, particularly examples 45-49, wherein the tension member is woven through one or more cells in the frame in an in-and-out pattern.

Example 51. The implantable device of any example herein, particularly examples 45-50, wherein the frame is self-expanding.

Example 52. The implantable device of any example herein, particularly examples 45-50, wherein the frame is mechanically expandable and comprises one or more expansion and locking mechanisms.

Example 53. The implantable device of any example herein, particularly examples 45-50, wherein the frame is balloon-expandable.

Example 54. The implantable device of any example herein, particularly examples 45-53, wherein the tension member comprises at least one of wire, string, and cable.

Example 55. A method, comprising:

inserting a distal end of a delivery apparatus into the vasculature of a patient, the delivery apparatus releasably coupled to an implantable prosthetic device comprising a frame and a tension member extending circumferentially around at least a portion of the frame, the tension member having a first end portion releasably coupled to the frame and a second end portion configured to be coupled to a handle of the delivery apparatus;

advancing the prosthetic valve to a selected implantation site;

tensioning the tension member to retain the frame in a radially compressed configuration;

retracting a sheath of the delivery apparatus to expose the implantable prosthetic device; and radially expanding the prosthetic device while gradually releasing the tension in the tension member to allow the prosthetic valve to expand at a controlled rate.

Example 56. A method, comprising:

determining a first selected maximum diameter for an inflow end portion and a second selected maximum diameter for an outflow end portion of an implantable prosthetic device based at least in part on a patient's native anatomy, the prosthetic device comprising a frame having first restriction band extending around a circumference of the frame at the inflow end portion and a second restriction band extending around the circumference of the frame at the outflow end portion;

releasing the first restriction band such that it is expandable to the first selected maximum diameter;

releasing the second restriction band such that it is expandable to the second selected maximum diameter;

advancing the implantable prosthetic device to a selected implantation site inside the body of the patient; and radially expanding the prosthetic device such that the inflow end portion is at the first selected maximum diameter and the outflow end portion is at the second selected maximum diameter.

Example 57. The method of any example herein, particularly example 56, wherein the patient's native anatomy is determined using at least one of an angiogram and a CT-scan.

Example 58. The method of any example herein, particularly examples 56-57, wherein the selected maximum diameter of the inflow end portion is greater than the selected maximum diameter of the outflow end portion.

Example 59. The method of any example herein, particularly examples 56-57, wherein the selected maximum diameter of the inflow end portion is less than the selected maximum diameter of the outflow end portion.

Example 60. The method of any example herein, particularly examples 56-59, wherein the first restriction band comprises a plurality of belts each having a different maximum diameter and wherein releasing the first restriction band comprises severing any belt that has a maximum diameter less than the first selected maximum diameter.

Example 61. The method of any example herein, particularly examples 56-60, wherein the second restriction band comprises a plurality of belts each having a different maximum diameter and wherein releasing the second restriction band comprises severing any belt that has a maximum diameter less than the second selected maximum diameter.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims. We therefore claim all that comes within the scope and spirit of these claims.

We claim:

1. A belt for an implantable prosthetic device, comprising:

an annular body including a plurality of alternating peaks and valleys; and a plurality of discrete, circumferentially extending frangible members extending between at least one of adjacent peaks and adjacent valleys, wherein the annular body is radially expandable from a radially compressed configuration to a first diameter upon application of a radially outwardly directed force via an expandable implantable prosthetic device; and wherein a first frangible member of the plurality of frangible members is configured to break when the radially outwardly directed force exceeds a first predetermined threshold to allow radial expansion of the annular body to a second diameter.

2. The belt of claim 1, wherein a second frangible member of the plurality of frangible members is configured to break when the radially outwardly directed force exceeds a second predetermined threshold to allow radial expansion of the annular body to a third diameter.

3. The belt of claim 1, wherein the plurality of frangible members comprises wires.

4. The belt of claim 1, wherein each frangible member of the plurality of frangible members comprises at least one of a crack or a perforated region.

5. An assembly, comprising:

an implantable prosthetic device comprising a frame movable between a radially compressed configuration and a radially expanded configuration; and a belt extending circumferentially around the frame, the belt comprising an annular body including a plurality of alternating peaks and valleys and a plurality of discrete circumferentially extending frangible members extending between at least one of adjacent peaks and adjacent valleys;

wherein the annular body is movable between a radially compressed state and a radially expanded state; and wherein the belt is configured to radially expand to a first diameter when a first force below a predetermined threshold of force is applied and expand to a second diameter when a second force greater than the predetermined threshold of force is applied.

6. The assembly of claim 5, wherein a first frangible member of the plurality of frangible members is configured to break when the second force applied to the belt, allowing the belt to radially expand to the second diameter.

7. The assembly of claim 6, wherein the predetermined threshold of force is a first predetermined threshold of force, and wherein a second frangible member is configured to break when a force greater than a second predetermined threshold of force is applied to the belt, allowing the belt to radially expand to a third diameter.

8. The assembly of claim 7, wherein the second predetermined threshold of force is equal to the first predetermined threshold of force.

9. The assembly of claim 6, wherein the plurality of frangible members comprises wires.

10. The assembly of claim 6, wherein each frangible member of the plurality of frangible members comprises at least one of a crack or a perforated region.

11. The assembly of claim 6, wherein each frangible member of the plurality of frangible members comprises a strut portion and a thinner portion, the strut portion having a first width and the thinner portion having a second width smaller than the first width.

12. The assembly of claim 5, wherein a radial force applied by the prosthetic device can be determined based at least in part on the diameter of the prosthetic device.

13. The assembly of claim 5, wherein the prosthetic device is a prosthetic heart valve comprising a plurality of leaflets that regulate a flow of blood through the frame.

14. An assembly, comprising:
an implantable prosthetic device comprising a frame movable between a radially compressed configuration and a radially expanded configuration; and a belt extending circumferentially around the frame, the belt configured to radially expand to a first diameter when a first force below a predetermined threshold of force is applied and expand to a second diameter when a second force greater than the predetermined threshold of force is applied;

the belt further comprising an annular body including a plurality of alternating peaks and valleys, the annular body being movable between a radially compressed state and a radially expanded state;

wherein the belt comprises a plurality of frangible members, and wherein a first frangible member of the plurality of frangible members is configured to break when the second force applied to the belt, allowing the belt to radially expand to the second diameter; and wherein the distance between adjacent peaks of the plurality of alternating peaks and valleys is a first length when the annular body is in the radially compressed state, wherein the distance between adjacent peaks of the plurality of alternating peaks and valleys is a second length when the annular body is in the radially expanded state, and wherein the second length is greater than the first length.

* * * * *